(12) United States Patent
Sherwood et al.

(10) Patent No.: US 8,889,930 B2
(45) Date of Patent: Nov. 18, 2014

(54) PROCESS FOR PRODUCING CHLORINATED HYDROCARBONS

(71) Applicant: Axiall Ohio, Inc., Atlanta, GA (US)

(72) Inventors: Scott A. Sherwood, Plum, PA (US); Stephen Robert Lester, Pittsburgh, PA (US)

(73) Assignee: Axiall Ohio, Inc., Atlanta, GA (US)

( * ) Notice: Subject to any disclaimer, the term of this patent is extended or adjusted under 35 U.S.C. 154(b) by 0 days.

(21) Appl. No.: 14/060,957

(22) Filed: Oct. 23, 2013

(65) Prior Publication Data

US 2014/0206911 A1 Jul. 24, 2014

Related U.S. Application Data

(60) Provisional application No. 61/755,062, filed on Jan. 22, 2013, provisional application No. 61/789,786, filed on Mar. 15, 2013.

(51) Int. Cl.
| | |
|---|---|
| *C07C 17/10* | (2006.01) |
| *C07C 17/06* | (2006.01) |
| *C07C 17/23* | (2006.01) |
| *C07C 17/25* | (2006.01) |

(52) U.S. Cl.
CPC ............. *C07C 17/23* (2013.01); *C07C 17/10* (2013.01); *C07C 17/06* (2013.01); *C07C 17/25* (2013.01)
USPC ........................................................ 570/230

(58) Field of Classification Search
CPC .......... C07C 17/23; C07C 17/269; C07C 5/48
See application file for complete search history.

(56) References Cited

U.S. PATENT DOCUMENTS

| | | | |
|---|---|---|---|
| 2,765,349 | A | 10/1956 | Conrad |
| 2,894,044 | A | 7/1959 | Prill |
| 4,535,194 | A | 8/1985 | Woodard |
| 4,650,914 | A | 3/1987 | Woodard |
| 5,689,020 | A | 11/1997 | Boyce |
| 5,811,605 | A | 9/1998 | Tang et al. |
| 5,902,914 | A | 5/1999 | Rygas et al. |
| 6,187,978 | B1 | 2/2001 | Rygas et al. |
| 6,313,360 | B1 | 11/2001 | Wilson et al. |
| 6,500,995 | B1 | 12/2002 | Branam |
| 6,534,688 | B2 | 3/2003 | Klausmeyer |
| 6,548,719 | B1 | 4/2003 | Nair et al. |
| 6,720,466 | B2 | 4/2004 | Wilson et al. |
| 7,094,936 | B1 | 8/2006 | Owens et al. |
| 7,102,041 | B2 | 9/2006 | Tung |
| 8,034,251 | B2 | 10/2011 | Merkel et al. |
| 8,034,984 | B2 | 10/2011 | Merkel et al. |
| 8,058,486 | B2 | 11/2011 | Merkel et al. |

(Continued)

FOREIGN PATENT DOCUMENTS

| | | |
|---|---|---|
| CH | 207500 A | 11/1939 |
| EP | 0002021 A1 | 5/1979 |

(Continued)

*Primary Examiner* — Rosalynd Keys
*Assistant Examiner* — Jennifer C Sawyer
(74) *Attorney, Agent, or Firm* — The Webb Law Firm

(57) ABSTRACT

The preparation of chlorinated hydrocarbons, such as pentachloropropanes, such as 1,1,1,2,3-pentachloropropane, from tetrachloropropanes, such as 1,1,1,3-tetrachloropropane, in the presence of a polyvalent antimony compound that includes a pentavalent antimony compound, such as antimony pentachloride, is described. Also described are methods for preparing optionally chlorinated alkenes, such as, tetrachloropropenes, from chlorinated alkanes, such as pentachloropropanes, in the presence of ferric chloride and a polyvalent antimony compound that includes a pentavalent antimony compound.

29 Claims, 2 Drawing Sheets

(56) References Cited

U.S. PATENT DOCUMENTS

| | | |
|---|---|---|
| 8,063,257 B2 | 11/2011 | Ma et al. |
| 8,067,649 B2 | 11/2011 | Kopkalli et al. |
| 8,115,038 B2 | 2/2012 | Wilson et al. |
| 8,119,845 B2 | 2/2012 | Merkel et al. |
| 8,258,353 B2 | 9/2012 | Kruper, Jr. et al. |
| 8,258,355 B2 | 9/2012 | Merkel et al. |
| 8,304,589 B2 | 11/2012 | Fukuju et al. |
| 8,487,146 B2 | 7/2013 | Wilson et al. |
| 8,558,041 B2 | 10/2013 | Tirtowidjojo et al. |
| 8,581,011 B2 | 11/2013 | Tirtowidjojo et al. |
| 8,581,012 B2 | 11/2013 | Tirtowidjojo et al. |
| 8,614,363 B2 | 12/2013 | Wilson et al. |
| 2003/0028057 A1 | 2/2003 | Owens et al. |
| 2004/0225166 A1 | 11/2004 | Wilson et al. |
| 2005/0049443 A1 | 3/2005 | Wilson |
| 2005/0177012 A1 | 8/2005 | Cohn et al. |
| 2006/0122441 A1 | 6/2006 | Tung |
| 2007/0197842 A1 | 8/2007 | Mukhopadhyay et al. |
| 2008/0091053 A1 | 4/2008 | Tung et al. |
| 2009/0030249 A1 | 1/2009 | Merkel et al. |
| 2009/0216055 A1 | 8/2009 | Wilson et al. |
| 2011/0087056 A1 | 4/2011 | Tirtowidjojo et al. |
| 2011/0245548 A1 | 10/2011 | Merkel et al. |
| 2011/0269999 A1 | 11/2011 | Cook et al. |
| 2011/0270000 A1 | 11/2011 | Bektesevic et al. |
| 2011/0275723 A1 | 11/2011 | Hulse et al. |
| 2012/0035402 A1 | 2/2012 | Wilson et al. |
| 2012/0053374 A1 | 3/2012 | Fukuju et al. |
| 2012/0190902 A1 | 7/2012 | Nyberg |
| 2012/0289751 A1 | 11/2012 | Nose et al. |
| 2012/0310020 A1 | 12/2012 | Close et al. |
| 2012/0310021 A1 | 12/2012 | Close et al. |
| 2013/0012743 A1 | 1/2013 | Wilson et al. |
| 2013/0165705 A1 | 6/2013 | Hosaka et al. |
| 2013/0197282 A1 | 8/2013 | Markel et al. |

FOREIGN PATENT DOCUMENTS

| | | |
|---|---|---|
| EP | 0131560 A1 | 1/1985 |
| EP | 0131561 A1 | 1/1985 |
| EP | 2628719 A1 | 8/2013 |
| WO | 2008127940 A1 | 10/2008 |
| WO | 2009015304 A1 | 1/2009 |
| WO | 2009085862 A1 | 7/2009 |
| WO | 2011126620 A2 | 10/2011 |
| WO | 2012081482 A1 | 6/2012 |
| WO | 2012166393 A1 | 12/2012 |
| WO | 2012166394 A1 | 12/2012 |
| WO | 2012166759 A2 | 12/2012 |
| WO | 2012170239 A1 | 12/2012 |
| WO | 2013022676 A1 | 2/2013 |
| WO | 2013022677 A1 | 2/2013 |
| WO | 2013022806 A1 | 2/2013 |
| WO | 2013049744 A2 | 4/2013 |
| WO | 2013074394 A1 | 5/2013 |
| WO | 2013074414 A1 | 5/2013 |
| WO | 2013078035 A1 | 5/2013 |
| WO | 2013090421 A1 | 6/2013 |
| WO | 2013095699 A1 | 6/2013 |

US 8,889,930 B2

PROCESS FOR PRODUCING CHLORINATED HYDROCARBONS

CROSS REFERENCE TO RELATED PATENT APPLICATIONS

The present application is entitled and claims priority to U.S. Patent Application No. 61/755,062, filed on Jan. 22, 2013, and U.S. Patent Application No. 61/789,786, filed on Mar. 15, 2013, the disclosures of which are in each case incorporated herein by reference in their entirety.

FIELD

The present invention relates to methods of preparing chlorinated hydrocarbons, such as pentachloropropanes, such as 1,1,1,2,3-pentachloropropane, from tetrachloropropanes, such as 1,1,1,3-tetrachloropropane, and to methods for preparing optionally chlorinated alkenes, such as, tetrachloropropenes, from chlorinated alkanes, such as pentachloropropanes.

BACKGROUND

Chlorinated hydrocarbons are useful as feedstocks for the manufacture of fluorinated hydrocarbons, such as hydrofluoroolefins (HFOs). Hydrofluoroolefins can, for example, be used as, or as components of, refrigerants, polyurethane blowing agents, fire extinguishing agents, and foaming agents. For purposes of illustration, 1,1,1,2,3-pentachloropropane can be used as an intermediate in the manufacture of 1,1,2,3-tetrachloropropene, which is a feedstock for the preparation of HFOs, and in the preparation of the herbicide trichloroallyl diisopropyl thiocarbamate, which is commonly referred to as Triallate.

The preparation of chlorinated hydrocarbons typically involves reactions that can require a number of steps, extended periods of time to complete, and/or reduced reaction temperatures and related refrigeration equipment, which can have increased economic costs associated therewith. It would be desirable to develop new methods of forming chlorinated hydrocarbons that require less steps and/or reduced reaction times relative to existing methods.

SUMMARY

In accordance with some embodiments of the present invention, there is provided a method of preparing 1,1,1,2,3-pentachloropropane comprising, reacting 1,1,1,3-tetrachloropropane with a source of chlorine in the presence of a polyvalent antimony compound comprising a pentavalent antimony compound, thereby forming a product comprising 1,1,1,2,3-pentachloropropane.

In accordance with some further embodiments of the present invention, there is provided a method of forming an alkene product, which method comprises, heating a chlorinated alkane substrate in the presence of ferric chloride and a polyvalent antimony compound comprising a pentavalent antimony compound, thereby forming a product comprising the alkene product, wherein the alkene product optionally has at least one chlorine group covalently bonded thereto, and wherein the chlorinated alkane substrate and the alkene product each have a carbon backbone structure that is in each case the same.

In accordance with some additional embodiments of the present invention, there is provided a method of preparing 1,1,2,3-tetrachloropropene, which method comprises: (a) reacting, in a first reaction, 1,1,1,3-tetrachloropropane with a source of chlorine in the presence of a polyvalent antimony compound comprising a pentavalent antimony compound, thereby forming a crude product comprising 1,1,1,2,3-pentachloropropane and said pentavalent antimony compound; and (b) heating, in a second reaction, the crude product in the presence of ferric chloride, thereby forming a product comprising 1,1,2,3-tetrachloropropene.

In accordance with some further additional embodiments of the present invention, there is provided a method of preparing 1,1,2,3-tetrachloropropene, which method comprises: (a) reacting, in a first reaction, 1,1,1,3-tetrachloropropane with a source of chlorine in the presence of a pentavalent antimony compound comprising antimony pentachloride, thereby forming a crude product comprising 1,1,1,2,3-pentachloropropane, 1,1,1,3-tetrachloropropane, antimony pentachloride, and antimony trichloride; (b) distilling the crude product thereby forming, (i) a tops product comprising 1,1,3-tetrachloropropane and antimony pentachloride, and (ii) a bottoms product comprising 1,1,1,2,3-pentachloropropane and antimony trichloride; (c) introducing a source of chlorine into the bottoms product, thereby converting at least a portion of the antimony trichloride to antimony pentachloride, thereby forming a modified bottoms product; and (d) heating, in a second reaction, the modified bottoms product in the presence of ferric chloride, thereby forming a product comprising 1,1,2,3-tetrachloropropene.

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments of the invention are illustrated and described.

BRIEF DESCRIPTION OF THE DRAWINGS

In FIGS. 1 and 2 like characters refer to the same equipment, streams, and/or components, such as conduits, reaction streams, reactors, condensers, and distillation columns, as the case may be, unless otherwise stated.

DETAILED DESCRIPTION

Figure 1:
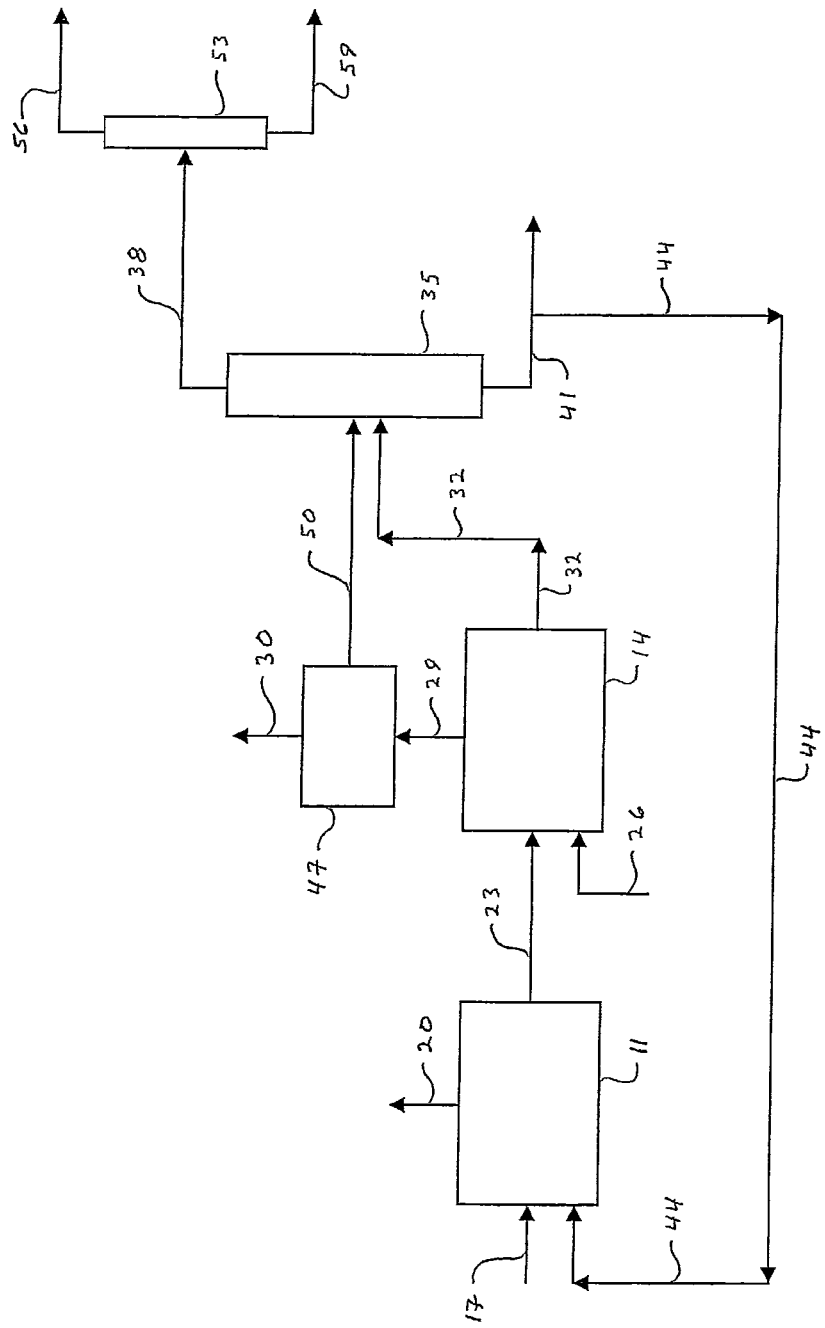
FIG. 1 is a schematic representation of a method of forming 1,1,2,3-tetrachloropropene in accordance with some embodiments of the present invention.

As used herein, the singular articles "a," "an," and "the" include plural referents unless otherwise expressly and unequivocally limited to one referent.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

Other than in the operating examples, or where otherwise indicated, all numbers expressing quantities of ingredients, reaction conditions, and so forth used in the specification and claims are to be understood as modified in all instances by the term "about."

All documents, such as but not limited to issued patents and patent applications, referred to herein, and unless otherwise indicated, are to be considered to be "incorporated by reference" in their entirety.

As used herein, the unit "psia" means pounds per square inch absolute, which is relative to vacuum.

As used herein, the unit "psig" means pounds per square inch gauge, which is relative to ambient atmospheric pressure.

As used herein, recitations of "alkyl" include "cycloalkyl" and/or "linear or branched alkyl." Recitations of "linear or branched" groups, such as linear or branched alkyl, are herein understood to include: a methylene group or a methyl group; groups that are linear, such as linear $C_2$-$C_{25}$ alkyl groups; and groups that are appropriately branched, such as branched $C_3$-$C_{25}$ alkyl groups.

The term "linear or branched alkyl" as used herein, in accordance with some embodiments, means linear or branched $C_1$-$C_{25}$ alkyl, or linear or branched $C_1$-$C_{10}$ alkyl, or linear or branched $C_2$-$C_{10}$ alkyl. Examples of alkyl groups from which the various alkyl groups of the present invention can be selected from, include, but are not limited to, methyl, ethyl, propyl, isopropyl, butyl, isobutyl, sec-butyl, tert-butyl, pentyl, neopentyl, hexyl, heptyl, octyl, nonyl and decyl.

The term "cycloalkyl" as used herein, in accordance with some embodiments, means alkyl groups that are appropriately cyclic, such as but not limited to, $C_3$-$C_{12}$ cycloalkyl (including, but not limited to, $C_5$-$C_7$ cycloalkyl) groups. Examples of cycloalkyl groups include, but are not limited to, cyclopropyl, cyclobutyl, cyclopentyl, cyclohexyl, and cyclooctyl. The term "cycloalkyl" as used herein in accordance with some embodiments also includes: bridged ring polycycloalkyl groups (or bridged ring polycyclic alkyl groups), such as but not limited to, bicyclo[2.2.1]heptyl (or norbornyl) and bicyclo[2.2.2]octyl; and fused ring polycycloalkyl groups (or fused ring polycyclic alkyl groups), such as, but not limited to, octahydro-1H-indenyl, and decahydronaphthyl.

As used herein, recitations of "alkenyl" include "cycloalkenyl" and/or "linear or branched alkenyl" and means groups having at least one ethylenically unsaturated group, that are not aromatic. The term "alkenyl" as used herein, in accordance with some embodiments, includes linear or branched $C_2$-$C_{25}$ alkenyl (including, but not limited to, linear or branched $C_2$-$C_{10}$ alkenyl). Examples of alkenyl groups include but are not limited to vinyl, allyl, propenyl, butenyl, pentenyl, and hexenyl. The term "cycloalkenyl" as used herein, in accordance with some embodiments, means alkenyl groups that are appropriately cyclic, such as but not limited to, $C_3$-$C_{12}$ cycloalkenyl (including, but not limited to, $C_5$-$C_7$ cycloalkenyl) groups. Examples of cycloalkenyl groups include, but are not limited to, cyclopropenyl, cyclobutenyl, cyclopentenyl, cyclohexenyl, cycloheptenyl, and cyclooctenyl.

As used herein, recitations of "alkynyl" include "cycloalkynyl" and/or "linear or branched alkynyl" and means groups having at least one carbon-carbon triple bond. The term "alkynyl" as used herein, in accordance with some embodiments, includes linear or branched $C_2$-$C_{25}$ alkynyl (including, but not limited to, linear or branched $C_2$-$C_{10}$ alkynyl). Examples of alkynyl groups include, but are not limited to, ethynyl, propynyl, butynyl (such as, 1-butynyl and 2-butynyl), pentynyl, hexynyl, heptynyl, and octynyl. The term "cycloalkynyl" as used herein, in accordance with some embodiments, means alkynyl groups that are appropriately cyclic, such as but not limited to, $C_8$-$C_{12}$ cycloalkynyl (including, but not limited to, $C_8$-$C_{10}$ cycloalkynyl) groups. Examples of cycloalkynyl groups include, but are not limited to, cyclooctynyl, and cyclononynyl.

As used herein, the term "aryl" includes cyclic aryl groups and polycyclic aryl groups. With some embodiments, aryl groups include, but are not limited to, $C_6$-$C_{18}$ aryl, such as $C_6$-$C_{10}$ aryl (including polycyclic aryl groups). Examples of aryl groups include, but are not limited to, phenyl, naphthyl, anthracenyl and triptycenyl.

As used herein, the term "alkane" includes "cycloalkane" and/or "linear or branched alkane." Recitations of "linear or branched alkane(s)" are herein understood to include: methane; alkanes that are linear, such as linear $C_2$-$C_{25}$ alkanes; and alkanes that are appropriately branched, such as branched $C_3$-$C_{25}$ alkanes.

The term "linear or branched alkane" as used herein, in accordance with some embodiments, includes linear or branched $C_1$-$C_{25}$ alkane, or linear or branched $C_1$-$C_{10}$ alkane, or linear or branched $C_2$-$C_{10}$ alkane. Examples of alkane groups from which the various alkanes of the present invention can be selected from, include, but are not limited to, methane, ethane, propane, isopropane, butane, isobutane, sec-butane, tert-butane, pentane, neopentane, hexane, heptane, octane, nonane and decane.

The term "cycloalkane" as used herein, in accordance with some embodiments, means alkanes that are appropriately cyclic, such as but not limited to, $C_3$-$C_{12}$ cycloalkane (including, but not limited to, $C_5$-$C_7$ cycloalkane). Examples of cycloalkane groups include, but are not limited to, cyclopropane, cyclobutane, cyclopentane, cyclohexane, cycloheptane, and cyclooctane. The term "cycloalkane" as used herein in accordance with some embodiments also includes: bridged ring polycycloalkanes (or bridged ring polycyclic alkanes), such as but not limited to, bicyclo[2.2.1]heptane (or norbornane) and bicyclo[2.2.2]octane; and fused ring polycycloalkanes (or fused ring polycyclic alkanes), such as, but not limited to, octahydro-1H-indenane, and decahydronaphthalene.

As used herein, recitations of "alkene" include "cycloalkene" and/or "linear or branched alkene" and means alkanes having at least one ethylenically unsaturated group, that are not aromatic. The term "linear or branched alkene" as used herein, in accordance with some embodiments, means linear or branched $C_2$-$C_{25}$ alkene (including, but not limited to, linear or branched $C_2$-$C_{10}$ alkene). Examples of alkenes include, but are not limited to, ethene, propene, butene, pentene, hexane, heptene, octane, nonene, and decene. The term "cycloalkene" as used herein, in accordance with some embodiments, means alkenes that are appropriately cyclic, such as but not limited to, $C_3$-$C_{12}$ cycloalkene (including, but not limited to, $C_5$-$C_7$ cycloalkene). Examples of cycloalkenes include, but are not limited to, cyclopropene, cyclobutene, cyclopentene, cyclohexene, and cyclooctene.

As used herein, recitations of "alkyne" include "cycloalkyne" and/or "linear or branched alkyne" and means cycloalkanes or alkanes having at least one carbon-carbon triple bond. The term "linear or branched alkyne" as used herein, in accordance with some embodiments, means linear or branched $C_2$-$C_{25}$ alkyne (including, but not limited to, linear or branched $C_2$-$C_{10}$ alkyne). Examples of alkynes include, but are not limited to, ethyne, propyne, butyne (such as, 1-butyne and 2-butyne), pentyne, hexyne, heptyne, and octyne. The term "cycloalkyne" as used herein, in accordance with some embodiments, means alkyne groups that are appropriately cyclic, such as but not limited to, $C_8$-$C_{12}$ cycloalkyne (including, but not limited to, $C_8$-$C_{10}$ cycloalkyne). Examples of cycloalkynes include, but are not limited to, cyclooctyne and cyclononyne.

As used herein, the term "aromatic," such as aromatic compound, includes cyclic aromatic and polycyclic aromatic. With some embodiments, aromatic compounds include, but are not limited to, $C_6$-$C_{18}$ aromatic compounds, such as $C_6$-$C_{10}$ aromatic compounds (including polycyclic aromatic compounds). Examples of aromatic compounds include, but are not limited to, benzene, naphthalene, anthracene and triptycene.

As used herein, the term "polyvalent antimony" and related terms, such as "polyvalent antimony compound," "polyvalent antimony catalyst," and "polyvalent antimony catalyst compound" include, but are not limited to, pentavalent antimony, trivalent antimony, and combinations thereof.

In accordance with some embodiments of the present invention, there is provided a method of preparing 1,1,1,2,3-pentachloropropane that involves, reacting 1,1,1,3-tetrachloropropane with a source of chlorine in the presence of a polyvalent antimony compound that includes a pentavalent antimony compound, thereby forming a product that includes 1,1,1,2,3-pentachloropropane. The reaction, with some embodiments is conducted in one or more suitable reactors. The method of preparing 1,1,1,2,3-pentachloropropane is, with some embodiments, performed as a batch method, a continuous method, and combinations thereof, such as combinations of one or more batch methods and one or more continuous methods.

The 1,1,1,3-tetrachloropropane, in accordance with some embodiments, can be obtained from any suitable source. With some embodiments, the 1,1,1,3-tetrachloropropane is formed by reacting carbon tetrachloride with ethylene in the presence of an iron chloride, iron metal, and a trialkylphosphate. Examples of iron chloride include, but are not limited to, ferric chloride and/or ferrous chloride. The term "iron metal" as used herein includes "metallic iron" and sources thereof. Examples of trialkylphosphates include, but are not limited to, triethylphosphates, tripropylphosphates and/or tributylphosphates. Preparation of 1,1,1,3-tetrachloropropane in accordance with such methods is described in, for example, U.S. Pat. Nos. 4,535,194, 4,650,914, and 8,487,146 B2 (such as at column 4, line 20 through column 5, line 55 thereof), and EP 0 131 561. Commercially available 1,1,1,3-tetrachloropropane material can, with some embodiments, include chemical components derived from the chemical reactants used to synthesize it. For example, commercially available 1,1,1,3-tetrachloropropane can include contaminating levels of carbon tetrachloride and other chlorinated hydrocarbons.

In accordance with some embodiments of the present invention, the 1,1,1,3-tetrachloropropane used in the present process is substantially free of chlorinated hydrocarbon contaminants, catalysts, other organic materials, such as alcohols with some embodiments, and is substantially free of water, such as containing less than 1000 ppm by weight of water with some embodiments.

The method of preparing 1,1,1,2,3-pentachloropropane from 1,1,1,3-tetrachloropropane in accordance with the present invention, is performed in the presence of a source of chlorine. The source of chlorine can be any source that provides chlorine for the reaction. With some embodiments, the source of chlorine does not have or cause any deleterious consequences on the reaction, such as promoting or generating undesirable byproducts, poisoning the polyvalent antimony catalyst, affecting the efficiency of the reaction, or affecting undesirably the temperature at which the chlorination reaction is conducted. The source of chlorine is liquid and/or gaseous chlorine ($Cl_2$), with some embodiments. In accordance with some embodiments, the source of chlorine is selected from chlorine ($Cl_2$), sulfuryl chloride ($SO_2Cl_2$), and combinations thereof, such as combinations of chlorine ($Cl_2$) and sulfuryl chloride ($SO_2Cl_2$).

With some embodiments, the source of chlorine is chlorine ($Cl_2$), and reacting 1,1,1,3-tetrachloropropane with the source of chlorine is conducted with a mole ratio of chlorine ($Cl_2$) to 1,1,1,3-tetrachloropropane of from 0.2:1 to 1.5:1, or from 0.2:1 to 1.1:1, or from 0.9:1 to 1.1:1, such as 1:1 (inclusive of the recited values).

In some instances, if an excessive amount of chlorine is used, such as greater than 1.5:1 (ratio of chlorine ($Cl_2$) to 1,1,1,3-tetrachloropropane), other pentachloropropanes, such as 1,1,1,3,3-pentachloropropane and over-chlorinated materials, can, with some embodiments, be produced as byproducts. Conversely, if the amount of chlorine used is significantly lower than 0.2:1 (ratio of chlorine ($Cl_2$) to 1,1,1,3-tetrachloropropane), an increased amount of unreacted material can, with some embodiments, result, which requires removal thereof from the reactor (such as by distillation), and disposal or reuse thereof, which can lead to higher capital and operating costs.

The method of preparing 1,1,1,2,3-pentachloropropane from 1,1,1,3-tetrachloropropane in accordance with the present invention, is performed in the presence of a polyvalent antimony compound, which includes a pentavalent antimony compound. With some embodiments, the polyvalent antimony compound(s) include(s) the pentavalent antimony compound(s) and optionally a trivalent antimony compound(s).

The pentavalent antimony compound, with some embodiments, includes one or more pentavalent antimony compounds represented by the following Formula (I), $$Sb(R^1)_a(Cl)_b \qquad (I)$$

With reference to Formula (I), the sum of a and b is 5, provided that b is at least 2, and $R^1$ independently for each a is selected from linear or branched alkyl, cyclic alkyl, and/or aryl.

With further reference to Formula (I), classes and examples of the linear or branched alkyl groups, cyclic alkyl groups, and aryl groups from which $R^1$ can be independently selected for each subscript a include, but are not limited to those classes and examples as recited previously herein, such as linear or branched $C_1$-$C_{25}$ alkyl groups, $C_3$-$C_{12}$ cycloalkyls, and/or $C_8$-$C_{18}$ aryl, and related examples thereof.

Examples of pentavalent antimony compounds that can be used with some embodiments of the present invention include, but are not limited to: antimony pentachloride; trialkyl antimony dichloride, such as tributyl antimony dichloride; and triaryl antimony dichloride, such as triphenyl antimony dichloride.

The trivalent antimony compound, includes, with some embodiments, one or more trivalent antimony compounds represented by the following Formula (II), $$Sb(R^2)_c(Cl)_d \qquad (II)$$

With reference to Formula (II), c is from 0 to 3, d is from 0 to 3, provided that the sum of c and d is 3, and $R^2$ independently for each c is selected from linear or branched alkyl, cyclic alkyl, and/or aryl.

With further reference to Formula (II), classes and examples of the linear or branched alkyl groups, cyclic alkyl groups, and aryl groups from which $R^2$ can be independently selected for each subscript c include, but are not limited to those classes and examples as recited previously herein, such as, $C_1$-$C_{25}$ alkyl groups, $C_3$-$C_{12}$ cycloalkyls, and/or $C_6$-$C_{18}$ aryl, and related examples thereof.

Examples of trivalent antimony compounds that can be used with some embodiments of the present invention include, but are not limited to: antimony trichloride, trialkyl antimony, such as tributyl antimony; and triaryl antimony, such as triphenyl antimony.

In accordance with some embodiments, the method of preparing 1,1,1,2,3-pentachloropropane includes forming at least a portion of the pentavalent antimony compound from a precursor of the pentavalent antimony compound. In accordance with some further embodiments, the precursor of the pentavalent antimony compound includes one or more trivalent antimony compounds represented by Formula (II) above. With some embodiments, the precursor of the pentavalent antimony compound is contacted with the source of chlorine, such as chlorine ($Cl_2$), such as in a reaction zone of a reactor, and at least a portion of the precursor of the pentavalent antimony compound is converted to a pentavalent antimony compound. For purposes of nonlimiting illustration, contact between antimony trichloride (as a precursor compound) and a source of chlorine, such as chlorine ($Cl_2$) results in conversion of at least a portion of the antimony trichloride to antimony pentachloride. In accordance with some embodiments, the method of the present invention is performed in the presence of both one or more pentavalent antimony compounds and one or more trivalent antimony compounds.

The precursor of the pentavalent antimony compound, with some embodiments, is selected from antimony trichloride, trialkyl antimony, triaryl antimony, and combinations of two or more thereof. With some additional embodiments, the precursor of the pentavalent antimony compound, is selected from antimony trichloride, triphenyl antimony, and combinations thereof.

The amount of polyvalent antimony compound used for the reaction that results in the formation of 1,1,1,2,3-pentachloropropane can, with some embodiments, vary widely. With some embodiments, the polyvalent antimony compound is present in an amount that is effective to catalyze the described reaction, such as being present in a catalytic amount. If more than an effective amount of polyvalent antimony compound is used, the cost of the polyvalent antimony compound itself and/or the disposal costs associated with used (or spent) polyvalent antimony compound can be taken into account, as such costs can affect (such as increase) the overall cost of the process, with some embodiments.

The effective amount of polyvalent antimony catalyst used can also depend on the other reaction conditions used, such as temperature, pressure, reactant flow rates, type of reaction vessel, etc. In the case of antimony pentachloride, which is a liquid at standard (or ambient) conditions, the amount of pentavalent antimony catalyst used for the liquid chlorination reaction can vary, with some embodiments, from 0.05 to 2 volume percent, based on the volume of the 1,1,1,3-tetrachloropropane reactant, such as 0.5 volume percent. With some embodiments, the amount of pentavalent antimony catalyst used can vary from 0.05 to 0.5 volume percent. A larger amount of pentavalent antimony catalyst in the reaction results in a reduced amount of time to complete the reaction, with some embodiments, compared to smaller amounts of pentavalent antimony catalyst.

In accordance with some embodiments of the present invention: (i) the polyvalent antimony compound is used in a free form, such as free of being supported on a solid support; and/or (ii) the polyvalent antimony compound is supported on a solid support (or solid carrier), such as a solid particulate support. With some further embodiments, the polyvalent antimony compound is supported on a solid support (or solid carrier), such as a solid particulate support. The solid support, with some embodiments, is selected from one or more silica supports, one or more alumina supports, one or more zeolite supports, one or more clay supports, one or more activated carbon supports, and combinations of two or more thereof.

Amorphous silica, such as precipitated silica can be used to support the polyvalent antimony compound (and/or a precursor material thereof), with some embodiments. The size of the amorphous silica powder can vary, and falls within a size range of from 60 to 200 mesh (U.S. screen size), with some embodiments. Any of the crystalline forms of silica can be used as a support, with some embodiments. With some embodiments, silica in one or more of the following crystalline forms is used: quartz; tridymite; and cristobalite.

Zeolites that can be used to support the polyvalent antimony compound (and/or a precursor material thereof) include, but are not limited to, the synthetic or naturally occurring aluminum and calcium, or aluminum and sodium silicates that are suitable for use in chlorination reactions. Such zeolites include, with some embodiments, those of the general type $Na_2O.2Al_2O_3.5SiO_2$ and $CaO.2Al_2O_3.5SiO_2$. Aluminas that can be used as a support for the polyvalent antimony compound (and/or a precursor material thereof) include those that are solid and suitable for use in chlorination reactions. Examples of such materials include the various crystalline forms of alumina, activated alumina, and calcined aluminas, which include the stable form of anhydrous alumina ($\alpha$-$Al_2O_3$). The particle size of the solid support can be in the range described for the amorphous precipitated silica, with some embodiments. The polyvalent antimony compound is chemically bonded to the support surface rather than simply deposited on the surface, with some embodiments, which can result in a reduction in the amount of polyvalent antimony compound lost during the chlorination reaction.

The supported polyvalent antimony compound can be prepared by techniques known to those skilled in the art, with some embodiments. For purposes of non-limiting illustration, antimony trichloride can be dissolved in toluene and refluxed overnight in the presence of the solid catalyst support, such as amorphous silica. Subsequently, the silica is cooled, separated from the liquid toluene, such as by filtration or some other suitable liquid-solid separation methods, washed with a solvent, such as toluene or absolute ethanol, and dried. While not intending to be bound by any theory, it is believed, with some embodiments, that at least some of the trivalent antimony supported on the solid support is converted in the presence of a source of chlorine, such as chlorine ($Cl_2$), to pentavalent antimony, which is also supported on the solid support.

In accordance with some embodiments of the present invention, reacting 1,1,1,3-tetrachloropropane with the source of chlorine in the presence of the polyvalent antimony compound is conducted at a temperature of at least 40° C. The temperature of the reactions, such as in the reaction zone, can range from 40° C. to 200° C., or from 50° C. to 120° C., or from 80° C. to 120° C., with some embodiments. A higher temperature within a described range, such as in the reaction zone, results in a faster chlorination reaction, but increased co-production of undesirable byproducts, such as hexachloropropanes, undesired pentachloropropanes, and materials generally referred to as heavies or bottom products, with some embodiments. As such, and with some embodiments, the production of 1,1,1,2,3-pentachloropropane is performed at a temperature range of 40° C. to 200° C., which can provide a desirable rate of reaction and minimize the number and amount of byproducts formed, with some embodiments.

The pressure (such as within the reaction zone) for the reaction of 1,1,1,3-tetrachloropropane with a source of chlorine in the presence of a polyvalent antimony compound so as to form 1,1,1,2,3-pentachloropropane, can vary, with some embodiments of the present invention. With some embodiments, the pressure is at least 1 psia. With some further embodiments, the pressure is from 1 psia to 500 psia, such as from 1 psia to 200 psia. Operation at high pressures, such as at least 100 psia, makes recovery of the hydrogen chloride (HCl) co-product easier, with some embodiments. Subatmospheric pressures can be used with some embodiments of the present invention. With some further embodiments, subatmospheric pressures are avoided.

In accordance with some embodiments of the present invention, reacting 1,1,1,3-tetrachloropropane with the source of chlorine in the presence of the polyvalent antimony compound, so as to form 1,1,1,2,3-pentachloropropane, is conducted at a temperature of at least 40° C., and a pressure of at least 1 psia.

In accordance with some further embodiments of the present invention, reacting 1,1,1,3-tetrachloropropane with the source of chlorine in the presence of the polyvalent antimony compound, so as to form 1,1,1,2,3-pentachloropropane, is conducted at a temperature of from 40° C. to 200° C., and a pressure is from 1 psia to 500 psia. With some embodiments, the chlorination methods of the present invention provide improved product selectivity and reduced byproduct production, compared to previous chlorination methods, such as those which are performed in the presence of ferric chloride or aluminum chloride.

Reacting 1,1,1,3-tetrachloropropane with a source of chlorine in the presence of the polyvalent antimony compound, so as to form 1,1,1,2,3-pentachloropropane, is conducted in the liquid phase and under substantially dry conditions, with some embodiments, because the presence of water, such as within the reaction zone, can result in either deactivation of the polyvalent antimony compound and/or the generation of hypochlorous acid (HOCl) from the reaction of chlorine with water, which can result in the generation of undesirable oxygenated by-products. While not intending to be bound by any theory, it is thought that the presence of water, such as in the reaction zone, can cause the production of hydrochloric acid, because of the reaction of water with chlorine and/or the hydrogen chloride co-product. Hydrochloric acid is an undesirable by-product, which can cause corrosion of vessels, piping, pumps and other equipment that would require the use of equipment made of more expensive hydrochloric acid resistant materials, with some embodiments. In accordance with some embodiments, the reactants, catalyst, etc. charged to the reactor (such as to the reaction zone) have less than 0.1 weight percent water, and which can be described as being substantially dry with some embodiments. The reactants and the reaction medium can contain less than 1000 ppm of water, such as from 5 to 1000 ppm of water, with some embodiments. Water that is present in the reactor before beginning the process (or water that enters the reactor subsequently, such as due to process interruptions) can be expunged by purging the reactor with a substantially dry or dried gas, such as dry nitrogen, hydrogen chloride, or chlorine.

The reaction time, for the reaction of 1,1,1,3-tetrachloropropane with a source of chlorine in the presence of the polyvalent antimony compound, so as to form 1,1,1,2,3-pentachloropropane, in accordance with some embodiments of the present invention can vary, and can depend on various parameters, such as the temperature at which the reaction is performed, the amount of antimony catalyst used, the nature of the reaction vessel, the desired degree of conversion of the 1,1,1,3-tetrachloropropane reactant, the chlorine feed rate, etc. According to some embodiments, the reaction time can vary from 0.5 to 12 hours, or from 3 to 5 hours, when the reaction is performed in a batch mode. Too long of a reaction time, due to for example restricting chlorine flow to the reactor, can result in an increased formation of undesirable dimerization byproducts, with some embodiments.

When performed in a continuous mode, the flow of reactants into the reactor, the reaction temperature (and pressure), and the volumetric flow of effluents withdrawn from the reactor are chosen to also achieve the desired degree of conversion of the 1,1,1,3-tetrachloropropane reactant to 1,1,1,2,3-pentachloropropane, while minimizing byproduct formation, in accordance with some embodiments. When conducted in a continuous mode, the average residence time in the reactor can vary from 0.5 to 12 hours, or from 3 to 5 hours, with some embodiments. The average residence time is defined as the reactor volume divided by the flow rate of 1,1,1,3-tetrachloropropane reactant into the reactor, with some embodiments.

With some embodiments, the reaction of 1,1,1,3-tetrachloropropane with a source of chlorine in the presence of the polyvalent antimony compound, so as to form 1,1,1,2,3-pentachloropropane is performed in a reactor that is fabricated from materials resistant to corrosion by the reactant materials, such as chlorine, the reaction mixture and the products, co-products and byproducts resulting from the reaction, such as hydrogen chloride and 1,1,1,2,3-pentachloropropane. Suitable materials from which the reactor can be constructed with some embodiments include, but are not limited to, glass, such as glass-lined steel vessels, nickel, nickel alloys, tantalum, fluorohydrocarbon polymers, such as HALAR-lined or TEFLON-lined vessels, such as polytetrafluoroethylene-lined vessels. The reactor vessel itself can be of any suitable design for chlorination reactions of the type described. With some embodiments, the reactor can be a vertical cylindrical vessel, or tubular in design, the design of which can accommodate the temperatures, pressures and corrosive environment associated with the chlorination process. The reactor can be packed with the supported catalyst, as in the case of a plug flow tubular reactor, or operated like a continuously stirred tank reactor, with some embodiments. If the catalyst is not supported by a solid carrier, but remains in liquid form, such as antimony pentachloride, or solid form, the reactor can have agitation means, such as agitators, to obtain intimate contact between the source of chlorine, 1,1,1,3-tetrachloropropane, and the polyvalent antimony compound, and to provide adequate contact of the reaction mixture with heat-transfer surfaces so as to enable adequate temperature control, with some embodiments.

The reaction of 1,1,1,3-tetrachloropropane with a source of chlorine in the presence of the polyvalent antimony compound, so as to form 1,1,1,2,3-pentachloropropane can be performed as a batch and/or continuous reaction, with some embodiments. In both modes, the reactor is associated with additional equipment, such as heating means to bring the reaction mixture to the desired reaction temperature, cooling means to remove exothermic heat from the reaction zone, such as by the cooling of the 1,1,1,3-tetrachloropropane reactant or by cooling coils within the reactor, heat exchanger means to control the temperature of gases and effluents removed from the reactor where required, gaseous effluent scrubbers, solid-liquid separators, and distillation columns to handle hydrogen chloride co-product off-gas, the separation of the principal product from any byproducts, and the separation of polyvalent antimony compound(s) withdrawn along with liquid heavy by-products.

In accordance with some embodiments, the reactants 1,1,1,3-tetrachloropropane and gaseous chlorine are introduced continuously into a cylindrical glass-lined reactor equipped with an agitator and containing 1,1,1,3-tetrachloropropane as the liquid reaction medium and polyvalent antimony compound. The temperature of the liquid reaction medium is controlled, such as cooled, by means of heat exchange coils in or around the reaction zone.

Hydrogen chloride co-product effluent (which can be in the form of a gaseous hydrogen chloride co-product effluent) is removed from the reactor overhead and separated, if necessary, from any chlorinated hydrocarbons carried with it, with some embodiments. The resultant recovered hydrogen chloride is substantially anhydrous and can either: (a) be further purified and used (or sold for use) in other applications; (b) dissolved in water and sold as hydrochloric acid; or (c) scrubbed with an alkali, such as sodium hydroxide, to neutralize the hydrogen chloride, with some embodiments. The resultant alkali metal chloride salt, such as sodium chloride, from such neutralization can be disposed of in an environmentally accepted manner or, in the case of sodium chloride, used as feedstock to a chlorine-caustic electrolytic cell circuit, with some further embodiments.

A crude product stream effluent that includes 1,1,1,2,3-pentachloropropane is removed from the reactor and optionally forwarded to a distillation zone containing one or more distillation columns (depending on the composition of the product stream and the design of the distillation column), with some embodiments. Polyvalent antimony compounds (such as, pentavalent antimony compounds and/or trivalent antimony compounds) and unreacted 1,1,1,3-tetrachloropropane separated from this crude product stream in a distillation zone can be recycled back to the reactor (where the reaction of 1,1,1,3-tetrachloropropane with a source of chlorine in the presence of the polyvalent antimony compound, so as to form 1,1,1,2,3-pentachloropropane, is conducted). Chlorine is optionally added to the distillation zone to maintain or increase the fraction of polyvalent antimony compound in the pentavalent state, which enhances the recovery of pentavalent antimony compound, in accordance with some embodiments of the present invention. If necessary, the 1,1,1,2,3-pentachloropropane product can be further purified in one or more additional distillation zones containing one or more distillation columns. Byproducts from the distillation zone(s) are recycled to the process or disposed of in an environmentally acceptable way, with some embodiments.

In accordance with some further embodiments of the present invention, there is provided a method of forming an alkene product. The method of forming the alkene product includes, with some embodiments, heating a chlorinated alkane substrate in the presence of ferric chloride and a polyvalent antimony compound comprising a pentavalent antimony compound, thereby forming a product comprising the alkene product. The alkene product optionally has at least one chlorine group covalently bonded thereto, and the chlorinated alkane substrate and the alkene product each have a carbon backbone structure that is in each case the same. This reaction can be referred to herein as a dehydrochlorination or cracking reaction. The terms dehydrochlorination or cracking (or terms of like import), as used herein, are used interchangeably to refer to the chemical rearrangement within a chlorinated alkane substrate that results in the creation of a double bond typically via the mechanism of the removal of a hydrogen atom and a chlorine atom from adjacent carbon atoms. The dehydrochlorination step is performed as a liquid phase reaction, with some embodiments.

During formation of the alkene product from the chlorinated alkane substrate, the carbon backbone of the chlorinated alkane substrate is not modified, and the carbon atoms of the chlorinated alkane substrate are not rearranged. As such, the chlorinated alkane substrate and the alkene product each have a carbon backbone structure that is in each case the same. For purposes of non-limiting illustration, when the chlorinated alkane substrate is a chlorinated propane, the corresponding alkene product is an optionally chlorinated propene. With some embodiments, the chlorinated alkane substrate has no carbon-carbon double bonds, and the alkene product has a single carbon-carbon double bond.

The alkene product is, with some embodiments, selected from those classes and examples of alkenes as described previously herein, which can further have at least one chlorine group (or atom) covalently bonded thereto. With some embodiments, the alkene product has one less chlorine atom covalently bonded thereto than the chlorinated alkane substrate. With some embodiments, the alkene product has one less chlorine atom covalently bonded thereto and one less hydrogen atom bonded thereto, compared to the chlorinated alkane substrate. For purposes of nonlimiting illustration, when the chlorinated alkane substrate is a pentachloropropane, the corresponding alkene product is a tetrachloropropene, with some embodiments. With some further embodiments: (i) the alkene product has one less chlorine atom covalently bonded thereto than the chlorinated alkane substrate; (ii) the alkene product has one less hydrogen atom covalently bonded thereto than the chlorinated alkane substrate; (iii) the alkene product has a single carbon-carbon double bond; and (iv) the chlorinated alkane substrate has no (or is free of) carbon-carbon double bonds. Examples of optionally chlorinated alkene products include, but are not limited to: optionally chlorinated linear or branched $C_2$-$C_{25}$ alkenes, such as optionally chlorinated linear or branched $C_2$-$C_{10}$ alkenes, or optionally chlorinated linear or branched $C_2$-$C_6$ alkenes; and optionally chlorinated $C_3$-$C_{12}$ cycloalkenes, such as optionally chlorinated $C_5$-$C_7$ cycloalkenes. Further examples of optionally chlorinated linear or branched alkene products include, but are not limited to, ethene, propene, butene, pentene, hexene, heptene, octene, nonene, and decene, which in each case optionally and independently include at least one chlorine group (or atom) bonded thereto. Further examples of optionally chlorinated cycloalkene products include, but are not limited to, cyclopropene, cyclobutene, cyclopentene, cyclohexene, cycloheptene, and cyclooctene, which in each case optionally and independently include at least one chlorine group (or atom) bonded thereto. Additional examples of alkene products include, but are not limited to, 1,1,2,3-tetrachloropropene, 1,2,3,3-tetrachloropropene, and 1,1,2,3,3-pentachloropropene.

The chlorinated alkane substrate (from which the alkene product is formed), with some embodiments, is selected from those classes and examples of alkanes as described previously herein, which further have at least one chlorine group (or atom) covalently bonded thereto. With some embodiments, the chlorinated alkane substrate is selected from those classes and examples of alkanes described previously herein, in which (i) at least one hydrogen thereof, and (ii) up to less than all of the hydrogens thereof are replaced with chlorine groups (or atoms) bonded to the carbon backbone structure thereof. With some further embodiments, the chlorinated alkane substrate is selected from those classes and examples of alkanes described previously herein, in which (i) at least one hydrogen thereof, and (ii) up to all of the hydrogens thereof are replaced with chlorine groups (or atoms) bonded to the carbon backbone structure thereof. Examples of chlorinated linear or branched alkane substrates include, but are not limited to, chlorinated linear or branched $C_2$-$C_{25}$ alkanes, or chlorinated linear or branched $C_2$-$C_{10}$ alkanes, or chlorinated linear or branched $C_2$-$C_{10}$ alkanes, or chlorinated linear or branched $C_2$-$C_6$ alkanes, which in each case independently have bonded thereto at least one chlorine group (or atom). Examples of chlorinated cycloalkane substrates include, but are not limited to, chlorinated $C_3$-$C_{12}$ cycloalkanes or chlorinated $C_5$-$C_7$ cycloalkanes, which each independently have bonded thereto at least one chlorine group (or atom). Further examples of chlorinated linear or branched alkane substrates include, but are not limited to, ethane, propane, isopropane, butane, isobutane, sec-butane, tert-butane, pentane, neopentane, hexane, heptane, octane, nonane, and decane, which in each case independently have bonded thereto at least one chlorine group (or atom). Further examples of chlorinated cycloalkane substrates include, but are not limited to, cyclopropane, cyclobutane, cyclopentane, cyclohexane, cycloheptane, and cyclooctene, which in each case independently have bonded thereto at least one chlorine group (or atom). Additional examples of chlorinated alkane substrates include, but are not limited to: 1,1,1,2,3-pentachloropropane; 1,1,2,3,3-pentachloropropane; and 1,1,1,2,3,3-hexachloropropane.

In accordance with some embodiments, the chlorinated alkane substrate is 1,1,1,2,3-pentachloropropane, and the alkene product is 1,1,2,3-tetrachloropropene.

With some embodiments, the polyvalent antimony compound, that is used in the formation of the alkene product, includes a pentavalent antimony compound and optionally a trivalent antimony compound. The pentavalent antimony compound can, with some embodiments, include one or more pentavalent antimony compounds represented by Formula (I), as described previously herein. The trivalent antimony compound can, with some embodiments, include one or more trivalent antimony compounds represented by Formula (II), as described previously herein.

The polyvalent antimony compound, that is used in the formation of the alkene product, includes, with some embodiments, both: (i) a pentavalent antimony compound, which includes antimony pentachloride; and (ii) a trivalent antimony compound, which includes antimony trichloride.

The alkene product and hydrogen chloride co-product are withdrawn from the dehydrochlorination reaction zone, and each purified, and recovered, with some embodiments. It has been observed that use of the described mixture of ferric chloride and polyvalent antimony compound reduces significantly the dehydrochlorination reaction time, compared to, using only ferric chloride as the dehydrochlorination catalyst. Further, the onset of significant conversion of chlorinated alkane substrate to alkene product occurs at temperatures that are 30° to 60° C. below the temperatures at which significant conversion occurs when using ferric chloride alone to catalyze the dehydrochlorination reaction, with some embodiments.

With some embodiments, ferric chloride and the polyvalent antimony compound are each independently present in a catalytic amount, during formation of the alkene product (or during the dehydrochlorination reaction). With some embodiments, the polyvalent antimony compound is present in an amount of from 0.01 percent by weight to 10 percent by weight, or from 0.1 percent by weight to 2 percent by weight, in each case based on weight of 1,1,1,2,3-pentachloropropane; and the ferric chloride is present in an amount of from 0.01 percent by weight to 10 percent by weight, or from 0.1 percent by weight to 5 percent by weight, in each case based on weight of 1,1,1,2,3-pentachloropropane.

In accordance with some embodiments of the present invention, the dehydrochlorination of the chlorinated alkane substrate is conducted in the liquid phase. With some further embodiments, when the chlorinated alkane substrate is 1,1,1,2,3-pentachloropropane and the alkene product is 1,1,2,3-tetrachloropropene, the dehydrochlorination of 1,1,1,2,3-pentachloropropane (so as to form 1,1,2,3-tetrachloropropene), is performed at temperatures of from 50° C. to 200° C., or from 100° C. to 165° C.

With some embodiments, the dehydrochlorination reaction is conducted at a pressure of at least 0.6 psia. With some further embodiments, the dehydrochlorination reaction is conducted at a pressure of from 0.6 psia to 215 psia, or from 1 psia to 115 psia. Use of relatively high pressures, such as at least 100 psia, allows the hydrogen chloride co-product to be recovered more easily. With some embodiments, subatmospheric dehydrochlorination reaction pressures are used (such as at least 0.6 psia). With some further embodiments, subatmospheric dehydrochlorination reaction pressures are avoided. With some embodiments, while not intending to be bound by any theory, and based on the evidence presently at hand, the pressure under-which the dehydrochlorination reaction is conducted, is not believed to materially affect the dehydrochlorination of the chlorinated alkane substrate, such as 1,1,1,2,3-pentachloropropane.

The weight ratio of ferric chloride to polyvalent antimony compound in the catalyst mixture used in the dehydrochlorination reaction can vary, with some embodiments of the present invention, such as from 1000:1 to 1:1000 {$FeCl_3$: polyvalent antimony compound}, such as from 1000:1 to 1:1000 {$FeCl_3$:(pentavalent antimony compound and optionally trivalent antimony compound)}, such as from 1000:1 to 1:1000 {$FeCl_3$:(antimony pentachloride and optionally antimony trichloride)}.

When the chlorinated alkane substrate is 1,1,1,2,3-pentachloropropane and the alkene product is 1,1,2,3-tetrachloropropene, heating 1,1,1,2,3-pentachloropropane in the presence of ferric chloride and the polyvalent antimony compound (so as to form 1,1,2,3-tetrachloropropene) is conducted at: temperatures of from 50° C. to 200° C., or from 100° C. to 165° C.; and a pressure of from 0.6 psia to 215 psia, or from 0.6 psia to 115 psia, with some embodiments.

When the chlorinated alkane substrate is 1,1,1,2,3-pentachloropropane and the alkene product is 1,1,2,3-tetrachloropropene, heating 1,1,1,2,3-pentachloropropane in the presence of ferric chloride and the polyvalent antimony compound (so as to form 1,1,2,3-tetrachloropropene) is conducted with a mole ratio of ferric chloride to polyvalent antimony compound of from 1000:1 to 1:1000.

Any reactor that is of suitable design to accommodate the dehydrochlorination reaction and the temperature, pressure and corrosive environment of the reactant materials, polyvalent antimony compound(s), ferric chloride, the reaction mixture, and the products, co-products and byproducts resulting from the reaction, such as hydrogen chloride and 1,1,2,3-tetrachloropropene, can be used to perform the dehydrochlorination of the chlorinated alkane substrate so as to form the corresponding alkene product. Examples of suitable reactor designs include vertical cylindrical vessels or tubular, such as plug-flow, reactors fabricated from appropriate materials of construction, such as corrosion resistant materials. Suitable materials of construction include carbon steel, glass, such as glass-lined steel vessels, nickel, nickel alloys, tantalum, fluorohydrocarbon polymers, such as, HALAR-lined or TEFLON-lined vessels, such as polytetrafluoroethylene-lined vessels.

The dehydrochlorination reactor can have one or more agitators for continuous agitation (or stirring) of the reaction medium in order to obtain intimate and adequate contact between the chlorinated alkane substrate and the polyvalent antimony compound(s) and ferric chloride, and to provide adequate contact of the reaction mixture with heat transfer surfaces to enable adequate temperature control. Agitation (or stirring) within the reactor can be accomplished with conventional and art-recognized agitators, static mixers, a circulation loop, etc. that are fabricated from suitable corrosion resistant materials of construction. Heat for the reaction can be applied internally or externally to the reactor, or alternatively, by heating the chlorinated alkane substrate.

The dehydrochlorination reaction is conducted in the liquid phase and under substantially dry conditions, with some embodiments, because the presence of water within the reactor (or reaction zone) can result in either deactivation of the polyvalent antimony compound(s) and/or ferric chloride, with some embodiments. The presence of water in the reactor (or reaction zone) can cause the production of hydrochloric acid, because of the reaction of water with ferric chloride, polyvalent antimony chloride compounds, and/or the hydrogen chloride co-product, with some embodiments. Hydrochloric acid is an undesirable byproduct that can cause corrosion of vessels, piping, pumps and other equipment that would require the use of equipment made of more expensive hydrochloric acid resistant materials, with some embodiments.

With the dehydrochlorination reaction, the reactants (or reaction components), such as, the chlorinated alkane substrate, polyvalent antimony compound(s), ferric chloride, optional solvent(s), etc., charged to the reactor (or reaction zone) are substantially dry, such as containing less than 0.1 weight percent water, with some embodiments. The reactants and the reaction medium contain less than 1000 ppm of water, such as from 5 to 1000 ppm of water, with some further embodiments. The presence of water in the reactor before beginning the process (or water that enters the reactor subsequently due, for example, to process interruptions) can be expunged by purging the reactor with a substantially dry or dried gas, such as dry nitrogen, hydrogen chloride or chlorine, in accordance with some embodiments.

The reaction time for the dehydrochlorination reaction that is performed in accordance with the presently described process can vary, and can depend on various parameters, such as the temperature at which the reaction is performed, the amount and ratio of the polyvalent antimony chloride and ferric chloride used, the type of reaction vessel, and the desired degree of conversion of the chlorinated alkane substrate, etc, with some embodiments. The dehydrochlorination reaction times can vary from 0.25 to 12 hours, or from 0.5 to 5 hours, when the reaction is performed in a batch mode, with some embodiments.

The dehydrochlorination reaction can, with some embodiments, be performed as a batch method, a continuous method, or a combination thereof, such as a combination batch method(s) and continuous method(s).

When the dehydrochlorination reaction is performed in a continuous mode, the flow of reactants into the reactor, the reaction temperature, the reaction pressure, and the volumetric flow of effluents withdrawn from the reactor are chosen to also achieve the desired degree of conversion of the chlorinated alkane substrate to the corresponding alkene product, in accordance with some embodiments. When conducted in a continuous mode, the average residence time can vary from 0.25 to 12 hours, or from 0.5 to 5 hours, with some embodiments. The average residence time is defined as the reactor volume divided by the flow rate of chlorinated alkane substrate in the dehydrochlorination reactor, in accordance with some embodiments.

With both the batch and continuous modes, and in accordance with some embodiments, the dehydrochlorination reactor is associated with additional process equipment, such as heating equipment (or means) to provide heat to the reaction zone, such as by the heating of the chlorinated alkane substrate or by heating coils within the reactor, heat exchanger means to control the temperature of gases and effluents removed from the reactor (where required), gaseous effluent scrubbers, solid-liquid separators, and distillation columns to handle the hydrogen chloride co-product off-gas, the separation of the principal product (i.e., the alkene product) from any byproducts, and the separation of the catalyst(s) withdrawn along with liquid heavy byproducts.

With some embodiments of the dehydrochlorination reaction of the present invention, hydrogen chloride co-product effluent (usually as a gaseous stream) is removed, with some embodiments, from the reactor overhead and separated, if necessary, from any uncondensed organic materials (such as alkene product and/or chlorinated alkane substrate) carried with it. In accordance with some further embodiments, the resultant recovered hydrogen chloride is substantially anhydrous and can either: (a) be further purified and used (or sold for use in other applications; or (b) dissolved in water and sold as hydrochloric acid; or (c) scrubbed with an alkali, such as sodium hydroxide, to neutralize the hydrogen chloride. The resultant alkali metal chloride salt, such as sodium chloride, can, with some embodiments, be disposed of in an environmentally accepted manner or, in the case of sodium chloride, used as feedstock to a chlorine-caustic electrolytic cell circuit.

In accordance with some embodiments of the dehydrochlorination reactions of the present invention, a product stream effluent including crude alkene product (such as 1,1,2,3-tetrachloropropene) is, with some embodiments, removed from the reactor and optionally forwarded to a distillation zone containing one or more distillation columns (depending on the composition of the product stream and the design of the distillation column) after separating any solid catalyst component(s) (if necessary) carried with it. Byproducts from the distillation zone are, with some embodiments, recycled to the process or disposed of in an environmentally accepted manner. In accordance with some embodiments, recovered polyvalent antimony compound(s), is optionally recycled back into the process. Substantially pure alkene product (such as 1,1,2,3-tetrachloropropene) is, with some embodiments obtained from the distillation zone, with some embodiments. By "substantially pure alkene product," with some embodiments, means the collected or isolated material includes at least 90 percent by weight, or at least 95 percent by weight, or at least 99 percent by weight, or at least 99.5 percent by weight, or at least 99.9 percent by weight of alkene product, based on total weight of the collected (or isolated) material.

With some embodiments, the alkene product, of the various methods of the present invention, includes one or more polyvalent antimony compounds and is a crude alkene product. The crude alkene product can, with some embodiments be used in further down-stream reactions, such as a hydrofluorination reaction, optionally after removal of iron chloride, such as ferric chloride, from the crude alkene product.

In accordance with some embodiments of the present invention, there is provided a method of forming 1,1,2,3-tetrachloropropene by a process that includes: in a first reaction, forming a crude product that includes 1,1,1,2,3-pentachloropropane and pentavalent antimony compound(s); and in a second reaction, heating the crude product of the first reaction in the presence of ferric chloride, so as to form a product that includes 1,1,2,3-tetrachloropropene.

The method of forming 1,1,2,3-tetrachloropropene includes, with some further embodiments: (a) reacting, in a first reaction, 1,1,1,3-tetrachloropropane with a source of chlorine in the presence of a polyvalent antimony compound that includes a pentavalent antimony compound, thereby forming a crude product that includes 1,1,1,2,3-pentachloropropane and the pentavalent antimony compound; and (b) heating, in a second reaction, the crude product in the presence of ferric chloride, thereby forming a product comprising 1,1,2,3-tetrachloropropene.

The first reaction is, with some embodiments, conducted in accordance with the chlorination reactions as described previously herein, which involve reacting 1,1,1,3-tetrachloropropane with a source of chlorine in the presence of a polyvalent antimony compound that includes a pentavalent antimony compound, thereby forming a product that includes 1,1,1,2,3-pentachloropropane. The second reaction is, with some embodiments, conducted in accordance with the dehydrochlorination reactions as described previously herein, which involves heating a chlorinated alkane substrate, such as 1,1,1,2,3-pentachloropropane, in the presence of ferric chloride and a polyvalent antimony compound that includes a pentavalent antimony compound, thereby forming a product that includes the alkene product, such as 1,1,2,3-tetrachloropropene.

The source of chlorine is, with some embodiments, selected from chlorine ($Cl_2$) and/or sulfuryl chloride ($SO_2Cl_2$), as described previously herein.

The pentavalent antimony compound can, with some embodiments, include one or more pentavalent antimony compounds represented by Formula (I) as described previously herein. With some embodiments, the pentavalent antimony compound includes antimony pentachloride.

With some additional embodiments, the polyvalent antimony compound of the first reaction optionally further includes one or more trivalent antimony compounds. The trivalent antimony compounds can, with some embodiments, include one or more trivalent antimony compounds represented by Formula (II) as described previously herein. With some embodiments, the trivalent antimony compound includes antimony trichloride.

For purposes of non-limiting illustration, the method of preparing 1,1,2,3-tetrachloropropene by a first reaction and a second reaction, in which the crude product of the first reaction is heated in the presence of ferric chloride in the second reaction, in accordance with some embodiments of the present invention, is described with reference to FIG. 1. With reference to FIG. 1, there is depicted a process assembly 3 that includes a chlorination reactor 11 and a dehydrochlorination reactor 14. Through one or more conduits, such as conduit 17, 1,1,1,3-tetrachloropropane, a source of chlorine, and a polyvalent antimony compound that includes a pentavalent antimony compound (and/or a precursor of the pentavalent antimony compound, as described previously herein) are introduced into chlorination reactor 11. The reaction components can be introduced into chlorination reactor 11 together and/or at different times in any appropriate order.

Within chlorination reactor 11, the first reaction is conducted, in which 1,1,1,3-tetrachloropropane is reacted with a source of chlorine in the presence of a polyvalent antimony compound that includes a pentavalent antimony compound. The first reaction, within chlorination reactor 11, results in the formation of a crude product that includes 1,1,1,2,3-pentachloropropane, the pentavalent antimony compound, and optionally one or more further polyvalent antimony compounds. As described previously herein, when a trivalent antimony compound is present in the first reaction, such as performed in reactor 11, at least a portion of the trivalent antimony compound is converted into the corresponding pentavalent antimony compound in the presence of the source of chlorine.

The 1,1,1,3-tetrachloropropane, source of chlorine, and polyvalent antimony compound that includes a pentavalent antimony compound are maintained within chlorination reactor 11, with some embodiments, at levels (or amounts) in accordance with the description provided previously herein. With some embodiments, the chlorination reaction is conducted within chlorination reactor 11 with a mole ratio of chlorine ($Cl_2$) to 1,1,1,3-tetrachloropropane of from 0.2:1 to 1.5:1 or from 0.2:1 to 1.1:1, and with a catalytic amount of polyvalent antimony compound. The polyvalent antimony compound can, with some embodiments, be present within chlorination reactor 11 in a non-supported form (such as in a liquid form) and/or in a supported form (such as supported on a solid support), as described previously herein.

Chlorination reactor 11 can, with some embodiments, be equipped with agitation components (not shown), such as an impeller, for mixing the contents of the chlorination reactor. Chlorination reactor 11 can, with some further embodiments, be equipped with one or more internal and/or one or more external heat exchangers (not shown) for purposes of controlling the temperature of the contents of the chlorination reactor.

The chlorination reaction is, with some embodiments, conducted within chlorination reactor 11 in accordance with the description as provided previously herein. With some embodiments, the chlorination reaction is conducted within chlorination reactor 11 at a temperature of at least 40° C., such as from 40° C. to 200° C., and a pressure of at least 1 psia, such as from 1 psia to 500 psia.

The first reaction conducted within chlorination reactor 11, with some embodiments, results in the formation of a crude product that includes 1,1,1,2,3-pentachloropropane and hydrogen chloride (HCl). With some embodiments, the hydrogen chloride is produced in a gaseous form, and is removed from chlorination reactor 11 through one or more appropriate conduits, such as conduit 20. The hydrogen chloride can, with some embodiments, be forwarded through conduit 20 for disposal and/or to one or more treatment apparatuses, such as a one or more scrubbers (not shown), as described previously herein, or further purified and used (or sold for use) in other applications.

The crude product formed within chlorination reactor 11, includes with some embodiments, 1,1,1,2,3-pentachloropropane, one or more pentavalent antimony compounds, such as antimony pentachloride, optionally one or more trivalent antimony compounds, such as antimony trichloride, and 1,1,1,3-tetrachloropropane. With some embodiments, the 1,1,1,3-tetrachloropropane is present in the crude product of the first reaction in an amount of less than 1 percent by weight, based on the total weight of the crude product.

The crude product formed within chlorination reactor 11, which includes 1,1,1,2,3-pentachloropropane and one or more pentavalent antimony compounds is forwarded through one or more appropriate conduits, such as conduit 23, to dehydrochlorination reactor 14. Within dehydrochlorination reactor 14 the second reaction is performed by heating the crude product (from the first reaction) in the presence of ferric chloride, so as to form a product that includes 1,1,2,3-tetrachloropropene.

Dehydrochlorination reactor 14 can, with some embodiments, be equipped with agitation components (not shown), such as an impeller, for mixing the contents of the dehydrochlorination reactor. Dehydrochlorination reactor 14 can, with some further embodiments, be equipped with one or more internal heat exchangers and/or one or more external heat exchangers (not shown) for purposes of controlling the temperature of the contents of the dehydrochlorination reactor.

The second reaction, which is performed in dehydrochlorination reactor 14, is conducted, with some embodiments, in accordance with the description as provided previously herein with regard to the method of forming an alkene product, such as 1,1,2,3-tetrachloropropene from 1,1,1,2,3-pentachloropropane. In accordance with some embodiments, the second reaction is performed in dehydrochlorination reactor 14 at a temperature of at least 50° C., such as from 50° C. to 200° C., and a pressure of at least 0.6 psia, such as from 0.6 psia to 215 psia. With some further embodiments, the second reaction is conducted in the dehydrochlorination reactor 14 with a mole ratio of ferric chloride to polyvalent antimony compound of from 1000:1 to 1:1000.

Ferric chloride can, with some embodiments, be periodically or continuously introduced into dehydrochlorination reactor 14 through one or more appropriate conduits, such as conduit 26.

The second reaction conducted within dehydrochlorination reactor 14, which some embodiments, results in the co-production of hydrogen chloride (HCl). The hydrogen chloride, with some embodiments, is formed as gaseous hydrogen chloride, which is removed from chlorination reactor 14 by one or more appropriate conduits, such as conduit 29. The hydrogen chloride can, with some embodiments, be forwarded through conduit 29 for disposal and/or to one or more treatment apparatuses, such as a one or more scrubbers (not shown), as described previously herein, or further purified and used (or sold for use) in other applications.

The product formed from the second reaction that is conducted within dehydrochlorination reactor 14, and which includes 1,1,2,3-tetrachloropropene can, with some embodiments, be removed from dehydrochlorination reactor 14, such as through conduit 32, and forwarded to storage and/or additional processing steps, such as purification and/or isolation processing steps.

The product formed from the second reaction, includes, with some embodiments, 1,1,2,3-tetrachloropropene, antimony pentachloride, and antimony trichloride, and the method further includes, distilling the product, thereby forming: (i) a tops product including 1,1,2,3-tetrachloropropene; and (ii) a bottoms product including 1,1,1,2,3-pentachloropropane, antimony pentachloride, antimony trichloride. If present in the product of the second reaction and the bottoms product (of distillation), the antimony pentachloride is, with some embodiments, present in an amount of less than 100 ppm, by weight. With some embodiments, a further distillation apparatus, such as a flash distillation apparatus, is used to remove ferric chloride prior to the distillation of the product of the second reaction, as described in further detail herein.

With some embodiments, at least a portion of the bottoms product (which includes 1,1,1,2,3-pentachloropropane and antimony trichloride) is introduced into the first reaction.

With further reference to FIG. 1, a product of the second reaction, which is performed within dehydrochlorination reactor 14, which includes 1,1,2,3-tetrachloropropene, antimony pentachloride, and antimony trichloride is forwarded through conduit 32 to a first distillation column 35 where it is subjected to distillation. Distilling of such product within first distillation column 35 results in the formation of: (i) a tops product that includes 1,1,2,3-tetrachloropropene, which is removed from first distillation column 35 through a conduit 38; and (ii) a bottoms product that includes 1,1,1,2,3-pentachloropropane, optionally antimony pentachloride, and antimony trichloride, which is removed from first distillation column 35 through a conduit 41. The tops product that includes 1,1,2,3-tetrachloropropene can be forwarded through conduit 38 to a storage tank (not shown) and/or to further processing steps, such as further purification and/or isolation steps.

With some embodiments, a further distillation apparatus (not shown), such as a flash distillation apparatus, is included in-line with conduit 32 between dehydrochlorination reactor 14 and distillation column 35 for purposes of removing ferric chloride, so as to prevent the introduction of ferric chloride into distillation column 35.

With some embodiments, at least a portion of the bottoms product that includes 1,1,1,2,3-pentachloropropane, antimony pentachloride, and antimony trichloride that is removed from first distillation column 35 through conduit 41 is forwarded through conduit 44 and introduced into the first reaction, which is conducted in chlorination reactor 11. While not intending to be bound by any theory, it is believed that at least a portion of the antimony trichloride within the bottoms product that is introduced into the first reaction in chlorination reactor 11 is converted to antimony pentachloride in the presence of the source of chlorine that is present within chlorination reactor 11.

In accordance with some embodiments of the present invention, the second reaction is conducted at a temperature and a pressure whereby at least a portion of the product is converted to a vaporous product that includes vaporous 1,1,2,3-tetrachloropropene. The method of the present invention then further includes: (i) removing vaporous product that includes vaporous 1,1,2,3-tetrachloropropene from the second reaction; and (ii) condensing the vaporous product removed from the second reaction into liquid product that includes liquid 1,1,2,3-tetrachloropropene. The formation of the vaporous product, and removal and condensation thereof is with some embodiments referred to as a reactive distillation process, which with some further embodiments is conducted continuously.

For purposes of non-limiting illustration of embodiments of the present invention, in which the second reaction is conducted so as to form a vaporous product, which is removed and condensed, further reference to FIG. 1 is made. The second reaction, which is conducted within dehydrochlorination reactor 14, is conducted at a temperature and a pressure whereby at least a portion of the product is converted to a vaporous product that includes 1,1,2,3-tetrachloropropene. The temperature and pressure can, with some embodiments, be selected from those temperatures, pressures and ranges as discussed previously herein. With some embodiments, the second reaction is conducted at a temperature of from 50° C. to 200° C., and a pressure of from 0.6 psia to 215 psia.

The vaporous product, which includes 1,1,2,3-tetrachloropropene, is removed from the second reaction and the dehydrochlorination reactor 14 through one or more appropriate conduits, such as conduit 29. With some embodiments, when vaporous product is removed through conduit 29, product of the second reaction is not removed through conduit 32. With some further embodiments, when vaporous product is removed through conduit 29, some product of the second reaction is also removed through conduit 32. With some embodiments of the present invention, reactor 14 is periodically purged to remove spent materials therefrom, such as, but not limited to, spent iron compounds, through one or more conduits (not shown).

The vaporous product, which includes 1,1,2,3-tetrachloropropene, is forwarded through conduit 29 and into condenser 47. Within condenser 47 the vaporous product is condensed into liquid product that includes liquid 1,1,2,3-tetrachloropropene. The condensed liquid product that includes liquid 1,1,2,3-tetrachloropropene is removed from condenser 47 through one or more appropriate conduits, such as through conduit 50. The condensed liquid product can, with some embodiments, be forwarded through conduit 50 to a storage tank (not shown), and/or to further processing steps, such as isolation and/or purification steps. With some embodiments, the condensed liquid product is removed from condenser 47 and forwarded through conduit 50 to first distillation column 35, in which the condensed liquid product is distilled so as to form a tops product that includes 1,1,2,3-tetrachloropropene, which is removed from first distillation column 35 and forwarded through conduit 38, and a bottoms product that includes other materials, which is removed from first distillation column 35 and forwarded through conduit 41.

As discussed previously herein, the second reaction conducted within dehydrochlorination reactor 14, which some embodiments, results in the co-production of gaseous hydrogen chloride (HCl). The gaseous hydrogen chloride is, with some embodiments, removed from dehydrochlorination reactor 14 and forwarded through conduit 29 and into condenser 47. Condenser 47 is, with some embodiments, operated under conditions such that the gaseous hydrogen chloride, introduced therein through conduit 29, does not condense. Gaseous hydrogen chloride thus, with some embodiments, passes through condenser 47 and is removed therefrom through conduit 30.

With some embodiments, the vaporous product of the second reaction formed within dehydrochlorination reactor 14 includes, vaporous 1,1,2,3-tetrachloropropene, vaporous 1,1,1,2,3-pentachloropropane, vaporous antimony pentachloride, and vaporous antimony trichloride. This multicomponent vaporous product is, with some embodiments, removed from the second reaction and dehydrochlorination reactor 14 through conduit 29 and forwarded through conduit 29 into condenser 47. Within condenser 47, the multicomponent vaporous product is condensed into a multicomponent liquid product that includes liquid 1,1,2,3-tetrachloropropene, liquid 1,1,1,2,3-pentachloropropane, liquid antimony pentachloride, and liquid antimony trichloride. The condensed multicomponent liquid product, with some embodiments, is removed from condenser 47 and forwarded through conduit 50 to a storage tank (not shown) and/or to further processing steps, such as isolation and/or purification steps.

With some embodiment, the condensed multicomponent liquid product, is removed from condenser 47 and forwarded through conduit 50 to first distillation column 35. Within first distillation column 35, the condensed multicomponent liquid product is distilled so as to form: (i) a tops product that includes 1,1,2,3-tetrachloropropene; and (ii) a bottom product that includes 1,1,1,2,3-pentachloropropane, antimony trichloride, and antimony pentachloride. The tops product that includes 1,1,2,3-tetrachloropropene is removed from first distillation column 35 and forwarded through conduit 38 to a storage tank (not shown) and/or to further processing steps, as described previously herein. The bottoms product is removed from first distillation column 35 and forwarded through conduit 41 to a storage tank (not shown) and/or to further processing steps, as described previously herein. With some embodiments, at least a portion of the bottoms product removed from first distillation column 35 through conduit 41 is forwarded through conduit 44 to chlorination reactor 11 where it is introduced into the first reaction, as described previously herein.

The tops product that includes 1,1,2,3-tetrachloropropene, which is removed from first distillation column 35 through conduit 38 is, with some embodiments, forwarded through conduit 38 to a second distillation column 53. The tops product removed from first distillation column 35, with some embodiments, includes 1,1,2,3-tetrachloropropene and one or more materials having a boiling point lower than that of 1,1,2,3-tetrachloropropene, which are referred to as lights. With some embodiments, the lights include 1,1,3,3-tetrachloropropene, 1,1,3-trichloropropene, and/or 1,1,1,3-tetrachloropropane. Distillation of the tops product within second distillation column 53 results in the formation of: (i) a second tops product, which includes the lights and (ii) a second bottoms product, which includes purified 1,1,2,3-tetrachloropropene, which is removed from second distillation column 53 and forwarded through conduit 59. The second tops product, which contains the lights, is, with some embodiments, forwarded through conduit 56 to a storage tank (not shown) and/or to further processing and/or disposal. The second bottoms product which includes purified 1,1,2,3-tetrachloropropene, is, with some embodiments, forwarded through conduit 59 to a storage tank (not shown) and/or further processing steps.

The method of the present invention, which involves preparing 1,1,2,3-tetrachloropropene by a first reaction and a second reaction, in which the crude product of the first reaction is heated in the presence of ferric chloride in the second reaction, is, with some embodiments, conducted as a batch method and/or a continuous method.

The method of the present invention, which involves preparing 1,1,2,3-tetrachloropropene by a first reaction and a second reaction, in which the crude product of the first reaction is heated in the presence of ferric chloride in the second reaction, includes, with some embodiments, forming 1,1,1,3-tetrachloropropane (which is used in the first reaction) by reacting carbon tetrachloride with ethylene in the presence of an iron chloride, iron metal, and a trialkylphosphate, in accordance with the description provided previously herein.

In accordance with some embodiments of the present invention, 1,1,2,3-tetrachloropropene is prepared by a process that includes: forming, in a first reaction, a crude product that includes 1,1,1,2,3-pentachloropropane; distilling the crude product to form a bottoms product that includes 1,1,1,2,3-pentachloropropane and antimony trichloride; introducing a source of chlorine into the bottoms product, so as to convert at least a portion of the antimony trichloride to antimony pentachloride, and thereby forming a modified bottoms product; and heating, in a second reaction, the modified bottoms product in the presence of ferric chloride, so as to form a product that includes 1,1,2,3-tetrachloropropene.

The method of forming 1,1,2,3-tetrachloropropene includes, with some further embodiments: (a) reacting, in a first reaction, 1,1,1,3-tetrachloropropane with a source of chlorine in the presence of a pentavalent antimony compound that includes antimony pentachloride, thereby forming a crude product that includes 1,1,1,2,3-pentachloropropane, 1,1,1,3-tetrachloropropane, antimony pentachloride, and antimony trichloride; (b) distilling the crude product thereby forming, (i) a tops product that includes 1,1,1,3-tetrachloropropane and antimony pentachloride, and (ii) a bottoms product that includes 1,1,1,2,3-pentachloropropane and antimony trichloride; (c) introducing a source of chlorine into the bottoms product, thereby converting at least a portion of the antimony trichloride to antimony pentachloride, thereby forming a modified bottoms product; and (d) heating, in a second reaction, the modified bottoms product in the presence of ferric chloride, thereby forming a product that includes 1,1,2,3-tetrachloropropene.

The first reaction is, with some embodiments, conducted in accordance with the chlorination reactions as described previously herein, which involve reacting 1,1,1,3-tetrachloropropane with a source of chlorine in the presence of a polyvalent antimony compound that includes a pentavalent antimony compound, such as antimony pentachloride, thereby forming a product that includes 1,1,1,2,3-pentachloropropane. The second reaction is, with some embodiments, conducted in accordance with the dehydrochlorination reactions as described previously herein, which involves heating a chlorinated alkane substrate, such as 1,1,1,2,3-pentachloropropane, in the presence of ferric chloride and a polyvalent antimony compound that includes a pentavalent antimony compound, such as antimony pentachloride, thereby forming a product that includes the alkene product, such as 1,1,2,3-tetrachloropropene.

The source of chlorine is, with some embodiments, selected from chlorine ($Cl_2$) and/or sulfuryl chloride ($SO_2Cl_2$), as described previously herein.

The pentavalent antimony compound can, with some embodiments, further include one or more pentavalent antimony compounds represented by Formula (I) as described previously herein.

With some additional embodiments, the first reaction optionally further includes one or more trivalent antimony compounds. The trivalent antimony compounds can, with some embodiments, include one or more trivalent antimony compounds represented by Formula (II) as described previously herein. With some embodiments, the trivalent antimony compound includes antimony trichloride.

Figure 2:
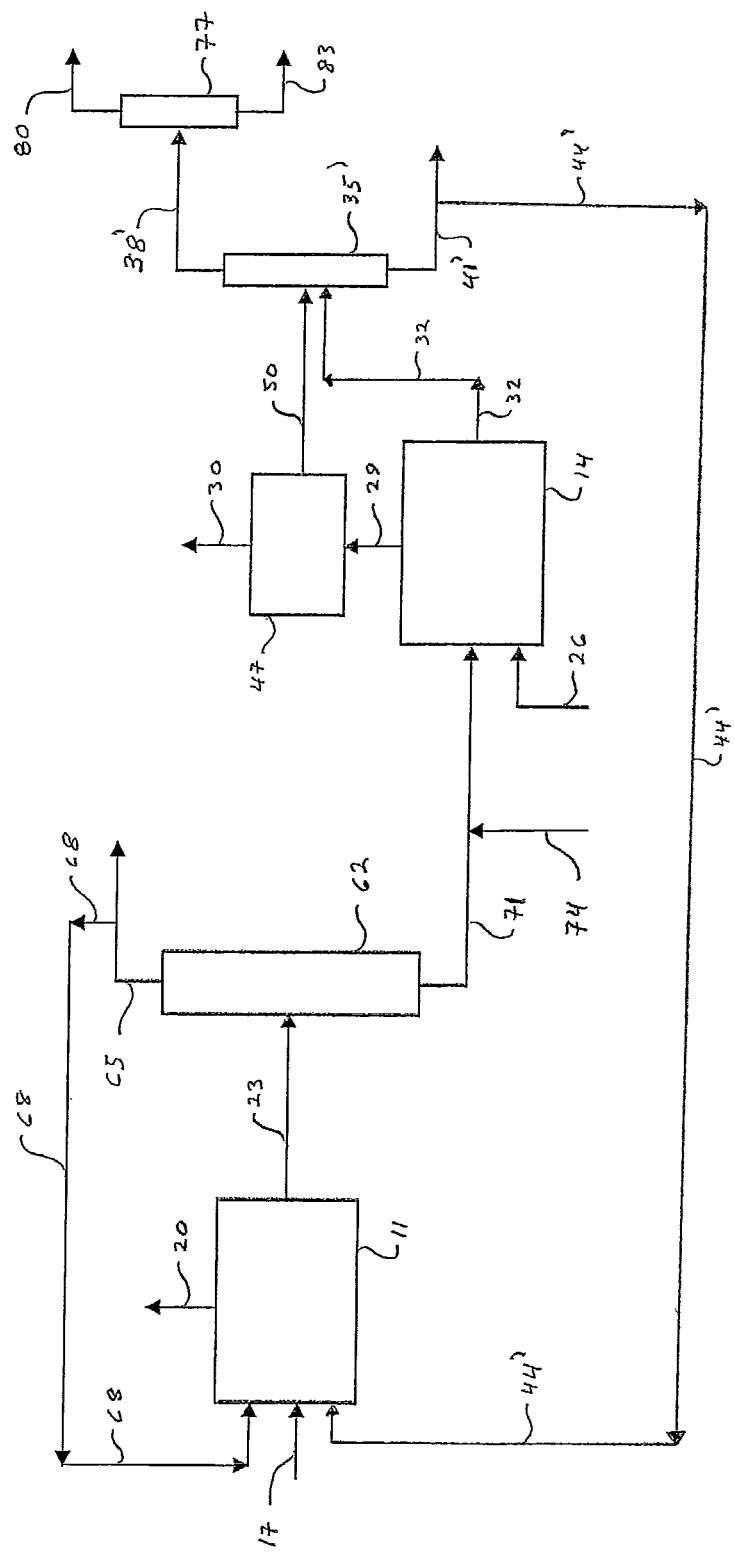
FIG. 2 is a schematic representation of a method of forming 1,1,2,3-tetrachloropropene in accordance with some further embodiments of the present invention.

For purposes of non-limiting illustration, the method of preparing 1,1,2,3-tetrachloropropene by a first reaction and a second reaction, in which a modified bottoms product, obtained by distillation of the crude product of the first reaction, is heated in the presence of ferric chloride in the second reaction, in accordance with some embodiments of the present invention, is described with reference to FIG. 2. With reference to FIG. 2, there is depicted a process assembly 5 that includes a chlorination reactor 11 and a dehydrochlorination reactor 14. Through one or more conduits, such as conduit 17, 1,1,1,3-tetrachloropropane, a source of chlorine, and a pentavalent antimony compound that includes antimony pentachloride (and/or a precursor of antimony pentachloride, as described previously herein) are introduced into chlorination reactor 11. The reaction components can be introduced into chlorination reactor 11 together and/or at different times in any appropriate order.

Within chlorination reactor 11, the first reaction is conducted, in which 1,1,1,3-tetrachloropropane is reacted with a source of chlorine in the presence of a pentavalent antimony compound that includes antimony pentachloride. The first reaction, within chlorination reactor 11 results in the formation of a crude product that includes 1,1,1,2,3-pentachloropropane, 1,1,1,3-tetrachloropropane, antimony pentachloride, and antimony trichloride.

The 1,1,1,3-tetrachloropropane, source of chlorine, and pentavalent antimony compound that includes antimony pentachloride are maintained within chlorination reactor 11, with some embodiments, at levels (or amounts) in accordance with the description provided previously herein. With some embodiments, the first reaction (or chlorination reaction) is conducted within chlorination reactor 11 with a mole ratio of chlorine ($Cl_2$) to 1,1,1,3-tetrachloropropane of from 0.2:1 to 1.5:1 or from 0.2:1 to 1.1:1, and with a catalytic amount of pentavalent antimony compound(s).

Chlorination reactor 11 can, with some embodiments, be equipped with agitation components (not shown), such as an impeller, for mixing the contents of the chlorination reactor. Chlorination reactor 11 can, with some further embodiments, be equipped with one or more internal and/or one or more external heat exchangers (not shown) for purposes of controlling the temperature of the contents of the chlorination reactor.

The first (or chlorination) reaction is, with some embodiments, conducted within chlorination reactor 11 in accordance with the description as provided previously herein. With some embodiments, the first (or chlorination) reaction is conducted within chlorination reactor 11 at a temperature of at least 40° C., such as from 40° C. to 200° C., and a pressure of at least 1 psia, such as from 1 psia to 500 psia.

The first reaction conducted within chlorination reactor 11, with some embodiments, results in the formation of the crude product and hydrogen chloride (HCl). With some embodiments, the hydrogen chloride is produced in a gaseous form, and is removed from chlorination reactor 11 through one or more appropriate conduits, such as conduit 20. The hydrogen chloride can, with some embodiments, be forwarded through conduit 20 for disposal and/or to one or more treatment apparatuses, such as a one or more scrubbers (not shown), as described previously herein, or further purified and used (or sold for use) in other applications.

The crude product formed within chlorination reactor 11, which includes 1,1,1,2,3-pentachloropropane, 1,1,1,3-tetrachloropropane, antimony pentachloride, and antimony trichloride, is forwarded through one or more appropriate conduits, such as conduit 23, to a first distillation column 62. Within first distillation column 62, the crude product of the first reaction is distilled so as to form; (i) a tops product that includes 1,1,1,3-tetrachloropropane and antimony pentachloride; and (ii) a bottoms product that includes 1,1,1,2,3-pentachloropropane and antimony trichloride.

The tops product, with some embodiments, is removed from first distillation column 62 and forwarded through conduit 65 to a storage tank (not shown) and/or one or more additional processing steps, such as isolation and/or purification steps. With some embodiments, at least a portion of the tops product, which includes 1,1,1,3-tetrachloropropane and antimony pentachloride, is introduced into the first reaction. With reference to FIG. 2, at least a portion of the tops product removed from first distillation column 62 through conduit 65 is forwarded through conduit 68 and introduced into the first reaction in chlorination reactor 11.

With further reference to FIG. 2, the bottoms product is removed from first distillation column 62 and forwarded through conduit 71. A source of chlorine is introduced into the bottoms product, with some embodiments, through a conduit 74 that intersects with conduit 71. Introduction of the source of chlorine into the bottoms product as it passes through conduit 71 results in conversion of at least a portion of the antimony trichloride to antimony pentachloride, thereby forming a modified bottoms product. The modified bottoms product includes, with some embodiments, 1,1,1,2,3-pentachloropropane, antimony pentachloride, and optionally antimony trichloride.

With some embodiments, the modified bottoms product is substantially free of the source of chlorine that was introduced into the bottoms product. Minimizing or eliminating the amount of source chlorine in the modified bottoms product is desirable, with some embodiments, because it can interfere with the formation of the desired 1,1,2,3-tetrachloropropene product. With some embodiments, the modified bottoms product includes less than 1000 ppm of the source of chlorine that was introduced into the bottoms product.

The modified bottoms product is further forwarded through conduit 71, past the intersection point with conduit 74, and introduced into dehydrochlorination reactor 14, where the second reaction is conducted.

The second reaction is, with some embodiments, conducted within dehydrochlorination reactor 14 of FIG. 2 in accordance with the description provided previously herein with regard to FIG. 1. Within dehydrochlorination reactor 14 the second reaction is performed by heating the modified bottoms product (obtained from distillation of the crude product of the first reaction) in the presence of ferric chloride, so as to form a product that includes 1,1,2,3-tetrachloropropene.

Dehydrochlorination reactor 14 of FIG. 2 can, with some embodiments, be equipped with agitation components (not shown), such as an impeller, for mixing the contents of the dehydrochlorination reactor. Dehydrochlorination reactor 14 can, with some further embodiments, be equipped with one or more internal and/or one or more external heat exchangers (not shown) for purposes of controlling the temperature of the contents of the dehydrochlorination reactor.

The second reaction, which is performed in dehydrochlorination reactor 14, is conducted, with some embodiments, in accordance with the description as provided previously herein with regard to the method of forming an alkene product, such as 1,1,2,3-tetrachloropropene from 1,1,1,2,3-pentachloropropane. In accordance with some embodiments, the second reaction is performed in dehydrochlorination reactor 14 of FIG. 2 at a temperature of at least 50° C., such as from 50° C. to 200° C., and a pressure of at least 0.6 psia, such as from 0.6 psia to 215 psia. With some further embodiments, the second reaction is conducted in the dehydrochlorination reactor 14 of FIG. 2 with a mole ratio of ferric chloride to polyvalent antimony compound of from 1000:1 to 1:1000.

Ferric chloride is, with some embodiments, periodically or continuously introduced into dehydrochlorination reactor 14 through one or more appropriate conduits, such as conduit 26.

The second reaction conducted within dehydrochlorination reactor 14, with some embodiments, results in the co-production of hydrogen chloride (HCl). The hydrogen chloride, with some embodiments, is formed as gaseous hydrogen chloride, which is removed from chlorination reactor 14 by one or more appropriate conduits, such as conduit 29. The hydrogen chloride can, with some embodiments, be forwarded through conduit 29 for disposal and/or to one or more treatment apparatuses, such as a one or more scrubbers (not shown), as described previously herein, or further purified and used (or sold for use) in other applications.

The product formed from the second reaction that is conducted within dehydrochlorination reactor 14, and which includes 1,1,2,3-tetrachloropropene can, with some embodiments, be removed from dehydrochlorination reactor 14, such as through conduit 32, and forwarded to storage and/or additional processing steps, such as purification and/or isolation processing steps.

The product formed from the second reaction, includes, with some embodiments, 1,1,2,3-tetrachloropropene, antimony pentachloride, and antimony trichloride, and the method further includes, distilling the product, thereby forming: (i) a second tops product including 1,1,2,3-tetrachloropropene; and (ii) a second bottoms product including 1,1,1,2,3-pentachloropropane and antimony trichloride. The second bottoms product can, with some embodiments, include antimony pentachloride, which if present, is typically present in an amount of less than 100 ppm by weight. With some embodiments, a further distillation apparatus, such as a flash distillation apparatus, is used to remove ferric chloride prior to the distillation of the product of the second reaction, as described in further detail herein.

With some embodiments, at least a portion of the second bottoms product (which includes 1,1,1,2,3-pentachloropropane and antimony trichloride) is introduced into the first reaction.

With further reference to FIG. 2, a product of the second reaction, which is performed within dehydrochlorination reactor 14, which includes 1,1,2,3-tetrachloropropene, antimony pentachloride, and antimony trichloride is forwarded through conduit 32 to a second distillation column 35' where it is subjected to distillation. Distilling of such product within second distillation column 35' results in the formation of: (i) a second tops product that includes 1,1,2,3-tetrachloropropene, which is removed from second distillation column 35' through a conduit 38'; and (ii) a second bottoms product that includes 1,1,1,2,3-pentachloropropane and antimony trichloride, which is removed from second distillation column 35' through a conduit 41'. The second tops product that includes 1,1,2,3-tetrachloropropene can be forwarded through conduit 38' to a storage tank (not shown) and/or to further processing steps, such as further purification and/or isolation steps.

With some embodiments, a further distillation apparatus (not shown), such as a flash distillation apparatus, is included in-line with conduit 32 between dehydrochlorination reactor 14 and second distillation column 35' for purposes of removing ferric chloride, so as to prevent the introduction of ferric chloride into second distillation column 35'.

With some embodiments, at least a portion of the second bottoms product that includes 1,1,1,2,3-pentachloropropane and antimony trichloride that is removed from second distillation column 35' through conduit 41' is forwarded through conduit 44' and introduced into the first reaction, which is conducted in chlorination reactor 11. While not intending to be bound by any theory, it is believed that at least a portion of the antimony trichloride within the second bottoms product that is introduced into the first reaction in chlorination reactor 11 is converted to antimony pentachloride in the presence of the source of chlorine that is present within chlorination reactor 11.

In accordance with some embodiments of the present invention, the second reaction is conducted at a temperature and a pressure whereby at least a portion of the product is converted to a vaporous product that includes vaporous 1,1,2,3-tetrachloropropene. The method then further includes: (i) removing vaporous product that includes vaporous 1,1,2,3-tetrachloropropene from the second reaction; and (ii) condensing the vaporous product removed from the second reaction into liquid product that includes liquid 1,1,2,3-tetrachloropropene. The formation of the vaporous product, and removal and condensation thereof is with some embodiments referred to as a reactive distillation process, which with some further embodiments is conducted continuously.

For purposes of non-limiting illustration of embodiments of the present invention, in which the second reaction is conducted so as to form a vaporous product, which is removed and condensed, further reference to FIG. 2 is made. The second reaction, which is conducted within dehydrochlorination reactor 14, is conducted at a temperature and a pressure whereby at least a portion of the product is converted to a vaporous product that includes 1,1,2,3-tetrachloropropene. The temperature and pressure can, with some embodiments, be selected from those temperatures, pressures and ranges as discussed previously herein. With some embodiments, the second reaction is conducted at a temperature of from 50° C. to 200° C., and a pressure of from 0.6 psia to 215 psia.

With reference to FIG. 2, the vaporous product, which includes 1,1,2,3-tetrachloropropene, is removed from the second reaction and the dehydrochlorination reactor 14 through one or more appropriate conduits, such as conduit 29. With some embodiments, when vaporous product is removed through conduit 29, the product of the second reaction is not removed through conduit 32. With some further embodiments, when vaporous product is removed through conduit 29, some of the product of the second reaction is also removed through conduit 32. With some embodiments of the present invention, dehydrochlorination reactor 14 is periodically purged to remove spent materials therefrom, such as, but not limited to, spent iron compounds, through one or more conduits (not shown).

With further reference to FIG. 2, the vaporous product, which includes 1,1,2,3-tetrachloropropene, is forwarded through conduit 29 and into condenser 47. Within condenser 47 the vaporous product is condensed into liquid product that includes liquid 1,1,2,3-tetrachloropropene. The condensed liquid product that includes liquid 1,1,2,3-tetrachloropropene is removed from condenser 47 through one or more appropriate conduits, such as through conduit 50. The condensed liquid product can, with some embodiments, be forwarded through conduit 50 to a storage tank (not shown), and/or to further processing steps, such as isolation and/or purification steps. With some embodiments, the condensed liquid product is removed from condenser 47 and forwarded through conduit 50 to second distillation column 35', in which the condensed liquid product is distilled so as to form a second tops product that includes 1,1,2,3-tetrachloropropene, which is removed from second distillation column 35' and forwarded through conduit 38', and a second bottoms product that includes other materials, which is removed from second distillation column 35' and forwarded through conduit 41'.

As discussed previously herein and with further reference to FIG. 2, the second reaction as conducted within dehydrochlorination reactor 14, with some embodiments, results in the co-production of gaseous hydrogen chloride (HCl). The gaseous hydrogen chloride is, with some embodiments, removed from dehydrochlorination reactor 14 and forwarded through conduit 29 and into condenser 47. Condenser 47 is, with some embodiments, operated under conditions such that the gaseous hydrogen chloride, introduced therein through conduit 29, does not condense. Gaseous hydrogen chloride thus, with some embodiments, passes through condenser 47 and is removed therefrom through conduit 30.

With some embodiments and with further reference to FIG. 2, the vaporous product of the second reaction formed within dehydrochlorination reactor 14 includes, vaporous 1,1,2,3-tetrachloropropene, vaporous 1,1,1,2,3-pentachloropropane, vaporous antimony pentachloride, and vaporous antimony trichloride. This multicomponent vaporous product is, with some embodiments, removed from the second reaction and dehydrochlorination reactor 14 through conduit 29 and forwarded through conduit 29 into condenser 47. Within condenser 47, the multicomponent vaporous product is condensed into a multicomponent liquid product that includes liquid 1,1,2,3-tetrachloropropene, liquid 1,1,1,2,3-pentachloropropane, liquid antimony pentachloride, and liquid antimony trichloride. The condensed multicomponent liquid product, with some embodiments, is removed from condenser 47 and forwarded through conduit 50 to a storage tank (not shown) and/or to further processing steps, such as isolation and/or purification steps.

With some embodiments and with further reference to FIG. 2, the condensed multicomponent liquid product, is removed from condenser 47 and forwarded through conduit 50 to second distillation column 35'. Within second distillation column 35', the condensed multicomponent liquid product is distilled so as to form: (i) a second tops product that includes 1,1,2,3-tetrachloropropene; and (ii) a second bottoms product that includes 1,1,1,2,3-pentachloropropane, antimony trichloride, and antimony pentachloride. The second tops product that includes 1,1,2,3-tetrachloropropene is removed from second distillation column 35' and forwarded through conduit 38' to a storage tank (not shown) and/or to further processing steps, as described previously herein. The second bottoms product is removed from second distillation column 35' and forwarded through conduit 41' to a storage tank (not shown) and/or to further processing steps, as described previously herein. With some embodiments, at least a portion of the second bottoms product removed from second distillation column 35' through conduit 41' is forwarded through conduit 44' to chlorination reactor 11 where it is introduced into the first reaction, as described previously herein.

With further reference to FIG. 2, the second tops product that includes 1,1,2,3-tetrachloropropene, which is removed from second distillation column 35' through conduit 38' is, with some embodiments, forwarded through conduit 38' to a third distillation column 77. The second tops product removed from second distillation column 35', with some embodiments, includes 1,1,2,3-tetrachloropropene and one or more materials having a boiling point lower than that of 1,1,2,3-tetrachloropropene, which are referred to as lights. With some embodiments, the lights include 1,1,3,3-tetrachloropropene, 1,1,3-trichloropropene, and/or 1,1,1,3-tetrachloropropane. Distillation of the second tops product within third distillation column 77 results in the formation of: (i) a third tops product, which includes the lights and (ii) a third bottoms product, which includes purified 1,1,2,3-tetrachloropropene, which is removed from third distillation column 77 and forwarded through conduit 83. The third tops product, which contains the lights, is, with some embodiments, forwarded through conduit 80 to a storage tank (not shown) and/or to further processing and/or disposal. The third bottoms product which includes purified 1,1,2,3-tetrachloropropene, is, with some embodiments, forwarded through conduit 83 to a storage tank (not shown) and/or further processing steps.

The method of preparing 1,1,2,3-tetrachloropropene by a first reaction and a second reaction, in which a modified bottoms product, obtained by distillation of the crude product of the first reaction, is heated in the presence of ferric chloride in the second reaction, in accordance with some embodiments of the present invention, is conducted as a continuous method and/or a batch method.

The method of the present invention, which involves preparing 1,1,2,3-tetrachloropropene by a first reaction and a second reaction, in which a modified bottoms product, obtained by distillation of the crude product of the first reaction, is heated in the presence of ferric chloride in the second reaction, in accordance with some embodiments of the present invention, includes with some embodiments, forming 1,1,1,3-tetrachloropropane (which is used in the first reaction) by reacting carbon tetrachloride with ethylene in the presence of an iron chloride, iron metal, and a trialkylphosphate, in accordance with the description provided previously herein.

The present invention is more particularly described in the examples that follow, which are intended to be illustrative only, since numerous modifications and variations therein will be apparent to those skilled in the art.

EXAMPLES

Example 1

Present Example 1 demonstrates a non-limiting embodiment of the present invention, in which 1,1,1,2,3-pentachloropropane was prepared under batch conditions, using antimony pentachloride ($SbCl_5$) as a catalyst.

To a 250 milliliter (mL) three-necked round bottom flask was charged 1,1,1,3-tetrachloropropane (147.1 grams) and antimony pentachloride (0.5 mL). The 250 mL three-necked round bottom flask was equipped with a chlorine inlet, magnetic stirring bar, 18 inch (45.72 cm) Vigreux column and a gas outlet, which was connected to a sodium hydroxide scrubber. The reaction flask was wrapped with insulating cloth to protect the reaction from ultraviolet light in order to suppress any free-radical chlorination that might occur. The amount of antimony pentachloride used represented 0.80 weight percent based on the amount of the tetrachloropropane reactant. The reaction mixture in the flask was heated to 70° C. by means of a heating mantle. Chlorine gas at 20° C. was added below the surface of the reaction mixture at a rate of approximately 0.32 grams per minute for three hours. Thereafter, the chlorine feed was stopped and the reaction vessel degassed with nitrogen. The crude reaction mixture was analyzed by means of gas chromatography (GC). The analysis showed the reaction mixture to contain 1,1,1,2,3-pentachloropropane with 81.3% selectivity, and 5 weight percent of 1,1,1,3-tetrachloropropane. The percent conversion of the tetrachloropropane reactant was calculated to be 95.1 percent.

Example 2

Present Example 2 demonstrates a non-limiting embodiment of the present invention, in which 1,1,1,2,3-pentachloropropane was prepared under batch conditions, using antimony trichloride ($SbCl_3$) as a precursor of antimony pentachloride ($SbCl_5$).

The procedure of Example 1 was followed, except that 143.5 grams of 1,1,1,3-tetrachloropropane was used, 0.90 grams of antimony trichloride was used (0.63 weight percent catalyst) and the reaction mixture was heated to 120° C. by means of the heating mantle. After three hours of chlorine feed, the flow of chlorine was stopped and the reaction vessel degassed with nitrogen. The crude reaction mixture (159.5 grams) was analyzed by GC and found to contain 1,1,1,2,3-pentachloropropane produced with 89% selectivity and 0.001 weight percent of 1,1,1,3-tetrachloropropane. The percent conversion of the tetrachloropropane reactant was calculated to be essentially 100 percent.

Example 3

Present Example 3 demonstrates a non-limiting embodiment of the present invention, in which 1,1,1,2,3-pentachloropropane was prepared under batch conditions, using triphenyl antimony ($Sb(C_6H_5)_3$) as a precursor of triphenyl antimony dichloride (($C_6H_5)_3SbCl_2$).

The procedure of Example 2 was followed except that 0.5 grams of triphenyl antimony was used (0.35 weight % of catalyst), and the chlorine was added over 5.5 hours. After completing the chlorine addition, the reaction vessel was degassed with nitrogen. The crude reaction mixture was analyzed by GC and found to contain 1,1,1,2,3-pentachloropropane produced with 81.2% selectivity. The percent conversion of the tetrachloropropane reactant was calculated to be essentially 100 percent.

Comparative Example 1

Present Comparative Example 1 was conducted in comparison to Example 1 above. In present Comparative Example 1, anhydrous ferric chloride was used as the catalyst in the absence of a polyvalent antimony compound, such as antimony pentachloride.

The procedure of Example 1 was followed except that anhydrous ferric chloride (0.64 grams) was used as the catalyst (0.45 weight percent of catalyst), and the reaction mixture was heated to 70° C. The chlorine feed (at 20° C.) was added over 2.25 hours. At the end of this time, the chlorine feed was stopped and the reaction vessel was degassed with nitrogen. The crude reaction mixture (132.4 grams) was analyzed by GC and found to contain 1,1,1,2,3-pentachloropropane produced with 58.7% selectivity, and 0.039 weight percent of 1,1,1,3-tetrachloropropane. The percent conversion of the tetrachloropropane was calculated to be 99.9 percent.

Example 4

Present Example 4 demonstrates a non-limiting embodiment of the present invention, in which 1,1,1,2,3-pentachloropropane was prepared under continuous conditions.

A feed solution of antimony trichloride (8.94 grams, 0.8 wt % $SbCl_5$ equivalent) and 1,1,1,3-tetrachloropropane (1,458.2 grams) was prepared by stirring the reagents with a magnetic stir bar in a one liter Erlenmeyer flask for 30 minutes.

To a 600-mL Nickel 200 autoclave was charged 230.9 grams of the feed solution. The contents of the autoclave were pressurized to 100 psig with nitrogen, heated to 80° C., and chlorine gas was introduced beneath the liquid surface when the temperature reached 80° C. After two hours of chlorine gas addition at 100 psig, additional feed solution (584.2 grams) was pumped into the autoclave at an overall average rate of 2.01 g/min. Chlorine gas addition (167 grams total) was continuously performed for a total of 410 minutes. A product mixture and HCl were removed via a dip tube with backpressure regulator to maintain a liquid level of about 180 mL in the autoclave and a pressure of about 100 psig. Upon shutdown, 795.7 grams of crude product mixture had been collected, and was determined by GC analysis to contain 54.8 wt % 1,1,1,2,3-pentachloropropane and 44.3 wt % 1,1,1,3-tetrachloropropane. Overall conversion was 51.2% with a selectivity of 99.1% to 1,1,1,2,3-pentachloropropane.

Example 5

Present Example 5 demonstrates a non-limiting embodiment of the present invention, in which 1,1,2,3-tetrachloropropene was prepared by way of a two-stage (first reaction-second reaction) serial batch process.

In a first reaction, 1,1,1,3-tetrachloropropane (143.5 grams) was charged to a 250 mL three-necked round bottom flask equipped with a thermocouple, magnetic stirring bar, chlorine inlet and an 18 inch (45.72 cm) Vigreux condenser connected to a sodium hydroxide scrubber. The tetrachloropropane was heated to 120° C. by means of a heating mantle, and 0.05 mL of antimony pentachloride was added to it. The mixture was magnetically stirred for one minute and then chlorine was introduced beneath the surface of the reaction mixture for 16 hours. After 13.66 hours had elapsed, an additional charge of antimony pentachloride (0.20 mL) was added to the reaction mixture, and the chlorine flow was continued. After the 16 hours of chlorine addition, the flow of chlorine was stopped. A crude 1,1,1,2,3-pentachloropropane product mixture was obtained containing 87.59 wt % 1,1,1,2,3,-pentachloropropane and no detectable 1,1,1,3-tetrachloropropane.

In a second reaction, the crude 1,1,1,2,3-pentachloropropane product mixture of the first reaction was cooled to 20° C. with nitrogen degassing to remove any excess chlorine. The cooled crude product mixture was then charged with 0.60 grams of anhydrous ferric chloride, so as to form a second reaction mixture, which was heated to 165° C. for two hours. Upon reaching a temperature of 123° C., the second reaction mixture evolved a copious amount of gas, as evidenced by bubbling in the sodium hydroxide scrubber. At the end of two hours, the resulting subsequent crude reaction product was cooled and analyzed by GC. It was found to contain 78.80 wt % 1,1,2,3-tetrachloropropene produced with 86.2% selectivity, and 0.03 weight percent of 1,1,1,2,3-pentachloropropane.

Comparative Example 2

Present Comparative Example 2 was conducted in comparison to the second reaction of Example 5 above.

A mixture of 1,1,1,2,3-pentachloropropane (66.0 grams) and anhydrous ferric chloride (0.10 grams) was charged to a 250 mL three-necked round bottom flask equipped with a condenser, thermocouple, mechanical stirrer and a gas outlet, which was connected to a water scrubber. The amount of ferric chloride catalyst used was 0.15 weight percent. The reaction mixture was heated over two days as follows: 150° C. for 2.25 hours, cooled to room temperature and stored under nitrogen, overnight, 160° C. for 3.17 hours, and 164° C. for 2.75 hours. The heating times as recited, include the time required to reach the new setpoint, either from room temperature or the previous setpoint. The reaction mixture was cooled and then flash vacuum distilled at pot temperatures ranging from 64° C. to 85° C. and a pressure of 120 Torr. The distillate (46.5 grams) was analyzed by GC and found to contain 1,1,2,3-tetrachloropropene produced with 98.7% selectivity and at an overall yield of 84.7 percent. It also contained 0.6 weight percent of 1,1,1,2,3-pentachloropropane. The percent conversion of the pentachloropropane reactant was calculated to be 99.4 percent.

Example 6

Present Example 6 demonstrates a non-limiting embodiment of the present invention, in which 1,1,2,3-tetrachloropropene was prepared under batch conditions from 1,1,1,2,3-pentachloropropane using a combination of ferric chloride and antimony pentachloride as the catalyst.

Fifty grams (50 g) of 1,1,1,2,3-pentachloropropane (having a purity of 96.94 wt %) and 0.1614 g of anhydrous ferric chloride (obtained from Fisher Scientific), and 25 microliters (µL) of antimony pentachloride (containing 0.059 g of antimony pentachloride, obtained from Aldrich) were combined in a 100-mL three-necked round-bottom flask equipped with a magnetic stirring bar, condenser attached to a water scrubber, thermocouple, and a heating mantle. The mixture was stirred and heated from room temperature to 165° C. Upon reaching 130° C., copious amounts of gas were evolved to the water scrubber and continued throughout the remainder of the experiment. After three hours, the mixture was cooled to room temperature and then sampled for gas chromatography analysis. The product was determined by GC analysis to contain 80.19 wt % of 1,1,2,3-tetrachloropropene and 16.74 wt % of 1,1,1,2,3-pentachloropropane, indicating a molar conversion of 85.1%.

Comparative Example 3

Present Comparative Example 3 provides a description of the batch preparation of 1,1,2,3-tetrachloropropene from 1,1,1,2,3-pentachloropropane using only ferric chloride as the catalyst.

Fifty grams (50 g) of 1,1,1,2,3-pentachloropropane (having a purity of 96.21 wt %) and 0.1676 g of anhydrous ferric chloride (obtained from Fisher Scientific) were combined in a 100-mL three-necked round-bottom flask equipped with a magnetic stirring bar, condenser attached to a water scrubber, thermocouple, and a heating mantle. The mixture was stirred and heated from room temperature to 165° C. After three hours, the mixture was cooled to room temperature and then sampled for GC analysis. The product was determined by GC analysis to contain 44.41 wt % of 1,1,2,3-tetrachloropropene and 52.40 wt % of 1,1,1,2,3-pentachloropropane, indicating a molar conversion of 50.4%).

Comparative Example 4

Present Comparative Example 4 provides a description of the batch preparation of 1,1,2,3-tetrachloropropene from 1,1,1,2,3-pentachloropropane using only ferric chloride as the catalyst.

Twenty grams (20 g) of 1,1,1,2,3-pentachloropropane (having a purity of 96.21 wt %) and 0.20 g of anhydrous ferric chloride (obtained from Fisher Scientific) were combined a 50-mL round-bottom flask equipped with a Claisen adapter, thermocouple, magnetic stirring bar, condenser attached to a water scrubber, and a heating mantle. The mixture was stirred and heated over two days as follows: 100° C. (3.85 hrs) then 110° C. (1.73 hrs); cooled to room temperature and stored over the weekend under nitrogen, 130° C. (1.50 hrs) then 150° C. (5.45 hrs). The heating times, as recited, include the time required to reach the new setpoint, either from room temperature or the previous setpoint. The mixture (14.9 g) was cooled to room temperature and then sampled for GC analysis. The product was determined by GC analysis to contain 99.35 wt % of 1,1,2,3-tetrachloropropene and 0.30 wt % of 1,1,1,2,3-pentachloropropane, indicating a conversion of 99.56% by weight (with regard to the starting amount of 1,1,1,2,3-pentachloropropane).

The following Table 1 provides a summary of Comparative Examples 2 and 4, and Example 4, for purposes of demonstrating the combination of desirable reaction time and conversion provided by the method of the present invention with regard to preparing 1,1,2,3-tetrachloropropene from 1,1,1,2,3-pentachloropropane using a combination of ferric chloride and antimony pentachloride as catalyst (Example 4) compared to using ferric chloride alone as the catalyst (Comparative Examples 2 and 4).

TABLE 1

| Example | Catalyst | Catalyst loading[1] | Temperature, ° C.[2] | Time Heated[3] | Conversion, %[4] |
|---|---|---|---|---|---|
| Comp 4 | FeCl$_3$ | 1 wt % | 150 | 12.53 hrs | 99.56 |
| Comp 2 | FeCl$_3$ | 0.15 wt % | 164 | 8.17 hrs | 99.40 |
| 4[5] | FeCl$_3$ SbCl$_5$ | 0.30 wt % 0.41 wt % | 165 | 2 hrs | 99.99 |

[1]Catalyst loading is based on weight of 1,1,1,2,3-pentachloropropane.
[2]The term "Temperature, ° C." means the maximum temperature of the reaction.
[3]The term "Time Heated" means the time from activation of the heating mantle to removal of the heating mantle from the reaction vessel.
[4]The percent conversion was determined by gas chromatography analysis.
[5]The second reaction of Example 4.

The Following Table 2 provides a summary of Comparative Example 3 and Example 6 for purposes of demonstrating the combination of desirable reaction time and conversion provided by the method of the present invention with regard to preparing 1,1,2,3-tetrachloropropene from 1,1,1,2,3-pentachloropropane using a combination of ferric chloride and antimony pentachloride as catalyst (Example 6) compared to using ferric chloride alone as the catalyst (Comparative Example 3), when the reactions are conducted at the same temperature (i.e., 165° C.), time (i.e., 3 hours), and catalyst loading (i.e., 0.33 wt % total).

Examples 8-10

The present Examples 8-10 demonstrate non-limiting embodiments of the present invention, in which crude 1,1,2,3-tetrachloropropene was prepared continuously under varying conditions. The procedure of Example 7 was followed, with the ferric chloride charge being modified. Reactor pressure was adjusted to change the temperature of the reactor, while still maintaining a constant pot level. Results of the experiment are summarized in the following Table 3.

TABLE 3

| Example | Catalyst Loading wt % FeCl$_3$[6] | Catalyst Loading Wt % SbCl$_5$[7] | Temperature (° C.)[8] | Pressure (Torr)[9] | Residence Time (minutes)[10] | 1,1,2,3-tetrachloropropene (wt %)[11] |
|---|---|---|---|---|---|---|
| 8 | 0.30 | 0.46 | 165.0 | 650 | 102 | 93.5 |
| 9 | 0.10 | 0.46 | 117.5 | 100 | 96 | 68.9 |
| 10 | 0.28 | 0.46 | 120.0 | 100 | 84 | 70.4 |

[6]Based on weight of crude 1,1,1,2,3-pentachloropropane in the initial charge.
[7]Analyzed concentration in crude 1,1,1,2,3-pentachloropropane.
[8]Average temperature at which the reaction was conducted.
[9]Average pressure at which the reaction was conducted.
[10]Average residence time, which was calculated in accordance with the equation shown in Example 7 herein.
[11]Based on the total weight of crude distillate product collected.

TABLE 2

| Example | Catalyst | Catalyst loading[1] | Temperature, ° C.[2] | Time Heated[3] | Conversion, %[4] |
|---|---|---|---|---|---|
| Comp 3 | FeCl$_3$ | 0.33 wt % | 165 | 3 hrs | 50.5 |
| 6 | FeCl3 SbCl5 | 0.32 wt % 0.10 wt % | 165 | 3 hrs | 85.2 |

(1), (2), (3), and (4) are as described with regard to TABLE 1.

Example 7

Present Example 7 demonstrates a non-limiting embodiment of the present invention, in which 1,1,2,3-tetrachloropropene was prepared under continuous conditions.

To a 250-mL three-necked round bottom flask was charged crude 1,1,1,2,3-pentachloropropane (157.8 grams, having a volume of about 100 mL, 98.4 wt % containing 0.46 wt % SbCl$_5$) and anhydrous ferric chloride (0.1730 grams). The 250-mL three-necked round bottom flask was equipped with a mechanical stirrer, addition funnel, Claisen adapter, thermocouple, and a distillation apparatus (which included a distillation head, condenser, and distillation receiver). Gases exiting the condenser were directed into a vacuum pump which discharged into a water scrubber. The three-necked round bottom flask and distillation apparatus were placed under vacuum (650 Torr) and heated via a heating mantle to 164-169° C. pot temperature. After about 80% conversion was achieve (as determined by measured weight gain in the water scrubber), additional crude 1,1,1,2,3-pentachloropropane (486.0 grams, having a volume of about 300 mL) was added dropwise to the contents of the three-necked round bottom flask over 271 minutes to maintain a constant pot level while collecting crude 1,1,2,3-tetrachloropropene distillate from the distillation apparatus. A total of 376.5 grams of crude distillate product was collected, and determined (by GC analysis) to contain 92.9 wt % 1,1,2,3-tetrachloropropene and 6.5 wt % 1,1,1,2,3-pentachloropropane. The average residence time was 90 min (100 mL/(300 mL/271 min)).

Example 11

Present Example 11 demonstrates a non-limiting embodiment of the present invention, in which a crude 1,1,2,3-tetrachloropropene product, that was prepared in accordance with Examples 4, 7, 8, 9, and 10, was distilled. About 10 percent of the crude 1,1,2,3-tetrachloropropene product was prepared in accordance with Example 4, and about 90 percent by weight of the crude 1,1,2,3-tetrachloropropene product was prepared in accordance with Examples 7, 8, 9, and 10, the percent weights in each case being based on the total weight of the crude 1,1,2,3-tetrachloropropene product.

A distillation apparatus was assembled using the following components: a 500-mL three-necked round bottom flask (which operated as a reboiler); a 10-tray, 2.54 cm Oldershaw vacuum-jacketed distillation column; a 2.54 cm Oldershaw vacuum-jacketed feed port; a 2.54 cm Oldershaw vacuum-jacketed packed section containing 115 cm of 0.16" Pro-Pak™ protruded Nickel packing; a swinging bucket product takeoff connected to a reflux timer, and a water-cooled condenser. The distillation apparatus was heated with a heating mantle controlled by a Variac voltage regulator.

The distillation apparatus was held at 100 Torr using a vacuum pump with a pressure controller. Over a period of 16 hours using a peristaltic pump, 2.15 kilograms (kg) of crude 1,1,2,3-tetrachloropropene product was pumped into the column of the distillation apparatus at the feed port, located between the Oldershaw and packed column sections. The crude 1,1,2,3-tetrachloropropene was prepared in accordance with some embodiments of the present invention and was determined, by GC analysis, to contain 81.0 wt % 1,1,2,3-tetrachloropropene, 17.7 wt % 1,1,1,2,3-pentachloropropane, 0.29 wt % SbCl$_3$, and 0.9 wt % of unidentified impurities. A distillate product, in an amount of 1.61 kg, was collected at a reflux ratio of 2:1. Bottoms were allowed to accumulate in the reboiler. Once feed pumping and product collection were stopped, the reflux ratio was dropped to 1:1, and 0.15 kg of additional distillate was collected. A residue, in an amount of 0.29 kg, remained in the reboiler.

The distillate product was determined, by GC analysis, to contain 99.65 wt % 1,1,2,3-tetrachloropropene, and by Inductively Coupled Plasma (ICP) analysis to contain antimony in an amount of less than 10 ppmw (parts per million by weight). The reboiler residue was determined, by GC analysis, to contain 94.6 wt % 1,1,1,2,3-pentachloropropane, and less than 0.1 wt % 1,1,2,3-tetrachloropropene, and by ICP analysis to contain 0.84 wt % antimony. Wet chemical analysis for antimony trichloride showed: less than 0.02 wt % of antimony trichloride in the distillate product; 0.66 wt % of antimony trichloride in the additional distillate; and 1.3 wt % antimony trichloride in the reboiler residue.

Example 12

Present Example 12 demonstrates a non-limiting embodiment of the present invention, in which reboiler residue containing antimony trichloride was recycled and used to form 1,1,1,2,3-pentachloropropane.

An aliquot (having a volume of about 50 mL) of the reboiler residue from Example 11 was passed through a syringe filter to remove a minor amount of solids. The resulting filtrate, in an amount of 67.53 grams (containing 1.10 wt % antimony trichloride), was mixed with 51.29 grams 1,1,1,3-tetrachloropropane (99% purity) to prepare a feed solution containing 0.64 wt % antimony trichloride. The feed solution was determined by GC analysis to contain 47.5 wt % 1,1,1,3-tetrachloropropane and 49.5 wt % 1,1,1,2,3-pentachloropropane.

The feed solution was charged to a 250-mL three-necked flask equipped with a thermocouple, magnetic stir-bar, chlorine sparger, and a 18" (45.72 cm) Vigreux condenser connected to a deionized water scrubber. The feed solution was heated to 100° C. using a Variac-controlled heating mantle attached to a temperature controller. A chlorine gas feed into the 250-mL three-necked flask was started when the temperature reached 70° C. Chlorine breakthrough was observed about 11 minutes into the run (after the chlorine gas feed was started). The chlorine gas flow rate was reduced and the breakthrough subsided. The chlorine gas feed was later returned to the initial higher flow rate without any additional breakthrough being observed. Chlorine gas in an amount totaling about 24.5 grams was fed to the 250-mL three-necked flask over a period of 4.3 hours. Hydrogen chloride, in an amount totaling 10.9 grams, was recovered in the scrubber. A product, totaling 120.6 grams, was collected and determined, by GC analysis, to contain 95.0 wt % 1,1,1,2,3-pentachloropropane and 0.015 wt % 1,1,1,3-tetrachloropropane.

The present invention has been described with reference to specific details of particular embodiments thereof. However, it is not intended that such details be regarded as limitations upon the scope of the invention except insofar as and to the extent that they are included in the accompanying claims.

What is claimed is:

1. A method of preparing 1,1,1,2,3-pentachloropropane comprising,
reacting 1,1,1,3-tetrachloropropane with a source of chlorine in the presence of a polyvalent antimony compound comprising a pentavalent antimony compound, thereby forming a product comprising 1,1,1,2,3-pentachloropropane.

2. The method of claim 1, wherein said source of chlorine is selected from chlorine ($Cl_2$), sulfuryl chloride, and combinations thereof.

3. The method of claim 1, wherein said polyvalent antimony compound comprises said pentavalent antimony compound and optionally a trivalent antimony compound, said pentavalent antimony compound comprising one or more pentavalent antimony compounds represented by the following Formula (I), $$Sb(R^1)_a(Cl)_b \qquad (I)$$

wherein the sum of a and b is 5, provided that b is at least 2, and
$R^1$ independently for each a is selected from the group consisting of linear, branched, or cyclic alkyl, and aryl, and
said trivalent antimony compound comprising one or more trivalent antimony compounds represented by the following Formula (II), $$Sb(R^2)_c(Cl)_d \qquad (II)$$

wherein the sum of c and d is 3, and
$R^2$ independently for each c is selected from the group consisting of linear, branched, or cyclic alkyl, and aryl.

4. The method of claim 3 further comprising, forming at least a portion of said pentavalent antimony compound from a precursor of said pentavalent antimony compound.

5. The method of claim 4, wherein said precursor of said pentavalent antimony compound comprises said trivalent antimony compound represented by Formula (II).

6. The method of claim 5, wherein said precursor of said pentavalent antimony compound is selected from the group consisting of antimony trichloride, trialkyl antimony, triaryl antimony, and combinations of two or more thereof.

7. The method of claim 6, wherein said precursor of said pentavalent antimony compound is selected from the group consisting of antimony trichloride, triphenyl antimony, and combinations thereof.

8. The method of claim 1, wherein said polyvalent antimony compound is supported on a solid support.

9. The method of claim 8, wherein said solid support is selected from the group consisting of silica supports, alumina supports, zeolite supports, and combinations of two or more thereof.

10. The method of claim 1, wherein said polyvalent antimony compound is present in a catalytic amount.

11. The method of claim 1, wherein said method is performed as a batch method, a continuous method, and combinations thereof.

12. The method of claim 1, wherein said source of chlorine is chlorine ($Cl_2$), and reacting 1,1,1,3-tetrachloropropane with said source of chlorine is conducted with a mole ratio of chlorine ($Cl_2$) to 1,1,1,3-tetrachloropropane of 0.2:1 to 1.5:1.

13. The method of claim 1 wherein, reacting 1,1,1,3-tetrachloropropane with said source of chlorine in the presence of said polyvalent antimony compound is conducted at a temperature of at least 40° C., and a pressure of at least 1 psia.

14. The method of claim 13, wherein said temperature is from 40° C. to 200° C., and said pressure is from 1 psia to 500 psia.

15. The method of claim 1, wherein said 1,1,1,3-tetrachloropropane is formed from reacting carbon tetrachloride with ethylene in the presence of an iron chloride, iron metal, and a trialkylphosphate.

16. A method of preparing 1,1,2,3,-tetrachloropropene comprising:
reacting, in a first reaction, 1,1,1,3-tetrachloropropane with a source of chlorine in the presence of a polyvalent antimony compound comprising a pentavalent antimony compound, thereby forming a crude product comprising 1,1,1,2,3-pentachloropropane and said pentavalent antimony compound; and heating, in a second reaction, said crude product in the presence of ferric chloride, thereby forming a product comprising 1,1,2,3-tetrachloropropene.

17. The method of claim 16, wherein said pentavalent antimony compound comprises one or more pentavalent antimony compounds represented by the following Formula (I),

wherein the sum of a and b is 5, provided that b is at least 2, and

R$^1$ independently for each a is selected from the group consisting of linear, branched, or cyclic alkyl, and aryl.

18. The method of claim 17, wherein said pentavalent antimony compound comprises antimony pentachloride.

19. The method of claim 18, wherein said product comprising 1,1,2,3-tetrachloropropene further comprises 1,1,1,2,3-pentachloropropane and antimony trichloride, and said method further comprises distilling said product thereby forming,
    a tops product comprising 1,1,2,3-tetrachloropropene, and
    a bottoms product comprising 1,1,1,2,3-pentachloropropane and antimony trichloride.

20. The method of claim 19 further comprising, introducing at least a portion of said bottoms product into said first reaction.

21. The method of claim 16, wherein said second reaction is conducted at a temperature and a pressure whereby at least a portion of said product is converted to a vaporous product comprising vaporous 1,1,2,3-tetrachloropropene, and said method further comprises,
    removing vaporous product comprising vaporous 1,1,2,3-tetrachloropropene from said second reaction, and
    condensing said vaporous product removed from said second reaction into liquid product comprising liquid 1,1,2,3-tetrachloropropene.

22. The method of claim 16, wherein said method is performed as a batch method, a continuous method, and combinations thereof.

23. The method of claim 16, wherein said 1,1,1,3-tetrachloropropane is formed by reacting carbon tetrachloride with ethylene in the presence of an iron chloride, iron metal, and a trialkylphosphate.

24. A method of preparing 1,1,2,3,-tetrachloropropene comprising:
    reacting, in a first reaction, 1,1,1,3-tetrachloropropane with a source of chlorine in the presence of a pentavalent antimony compound comprising antimony pentachloride, thereby forming a crude product comprising 1,1,1,2,3-pentachloropropane, 1,1,1,3-tetrachloropropane, antimony pentachloride, and antimony trichloride;
    distilling said crude product thereby forming,
        a tops product comprising 1,1,1,3-tetrachloropropane and antimony pentachloride, and
        a bottoms product comprising 1,1,1,2,3-pentachloropropane and antimony trichloride;
    introducing a source of chlorine into said bottoms product, thereby converting at least a portion of the antimony trichloride to antimony pentachloride, thereby forming a modified bottoms product; and
    heating, in a second reaction, said modified bottoms product in the presence of ferric chloride, thereby forming a product comprising 1,1,2,3-tetrachloropropene.

25. The method of claim 24, wherein said modified bottoms product is substantially free of said source of chlorine.

26. The method of claim 24 further comprising, introducing at least a portion of said tops product into said first reaction.

27. The method of claim 24, wherein said second reaction is conducted at a temperature and a pressure whereby at least a portion of said product is converted to a vaporous product comprising vaporous 1,1,2,3-tetrachloropropene, and said method further comprises,
    removing said vaporous product comprising vaporous 1,1,2,3-tetrachloropropene from said second reaction, and
    condensing said vaporous product removed from said second reaction into liquid product comprising liquid 1,1,2,3-tetrachloropropene.

28. The method of claim 24, wherein said method is performed as a continuous method, a batch method, and combinations thereof.

29. The method of claim 24, wherein said 1,1,1,3-tetrachloropropane is formed by reacting carbon tetrachloride with ethylene in the presence of an iron chloride, iron metal, and a trialkylphosphate.

* * * * *